(12) United States Patent
Adhisantoso et al.

(10) Patent No.: US 12,100,481 B2
(45) Date of Patent: Sep. 24, 2024

(54) SYSTEM AND METHOD OF EFFICIENT CODING AND DECODING OF CONTACT MATRICES

(71) Applicant: GOTTFRIED WILHELM LEIBNIZ UNIVERSITÄT HANNOVER, Hannover (DE)

(72) Inventors: Yeremia Gunawan Adhisantoso, Hannover (DE); Jörn Ostermann, Hannover (DE)

(73) Assignee: GOTTFRIED WILHELM LEIBNIZ UNIVERSITAT HANNOVER, Hannover (DE)

( * ) Notice: Subject to any disclaimer, the term of this patent is extended or adjusted under 35 U.S.C. 154(b) by 0 days.

(21) Appl. No.: 18/075,257

(22) Filed: Dec. 5, 2022

(65) Prior Publication Data
US 2023/0106805 A1    Apr. 6, 2023

Related U.S. Application Data

(60) Provisional application No. 63/252,225, filed on Oct. 5, 2021.

(51) Int. Cl.
*G16B 30/00*    (2019.01)
*G16B 40/20*    (2019.01)

(52) U.S. Cl.
CPC ............. *G16B 30/00* (2019.02); *G16B 40/20* (2019.02)

(58) Field of Classification Search
CPC ........ G16B 30/00; G16B 40/20; G16B 20/20; G16B 30/10
See application file for complete search history.

(56) References Cited

U.S. PATENT DOCUMENTS

| | | | |
|---|---|---|---|
| 2019/0222225 A1* | 7/2019 | Ahirwar | H04L 25/0224 |
| 2019/0371429 A1* | 12/2019 | Azab | G16B 20/10 |
| 2021/0090694 A1* | 3/2021 | Colley | G16H 15/00 |
| 2023/0183812 A1* | 6/2023 | Ki | G06N 3/04 702/19 |

* cited by examiner

*Primary Examiner* — Mark D Featherstone
*Assistant Examiner* — Kweku William Halm

(57) ABSTRACT

A system and method relate to encoding and decoding a contact matrix data structure. A system includes a processor and a computer-readable storage device storing a contact matrix data structure. The contact matrix data structure includes a header containing an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payloads.

30 Claims, 20 Drawing Sheets

200

| CHROM1 | START1 | END1 | CHROM2 | START2 | END2 | COUNT |
|---|---|---|---|---|---|---|
| CHR1 | 5000 | 10000 | CHR1 | 5000 | 10000 | 10 |
| CHR1 | 5000 | 10000 | CHR1 | 10000 | 13000 | 5 |
| CHR1 | 30000 | 35000 | CHR2 | 5000 | 10000 | 3 |
| CHR1 | 30000 | 35000 | CHR2 | 10000 | 15000 | 1 |

FIG. 2

| CHROM1 | START1 | END1 | CHROM2 | START2 | END2 | COUNT |
|---|---|---|---|---|---|---|
| CHR1 | 5000 | 10000 | CHR1 | 5000 | 10000 | 10 |
| CHR1 | 5000 | 10000 | CHR1 | 10000 | 13000 | 5 |

| CHROM1 | START1 | END1 | CHROM2 | START2 | END2 | COUNT |
|---|---|---|---|---|---|---|
| CHR1 | 30000 | 35000 | CHR2 | 5000 | 10000 | 3 |
| CHR1 | 30000 | 35000 | CHR2 | 10000 | 15000 | 1 |

| CHROM1 | START1 | END1 | CHROM2 | START2 | END2 | KR |
|---|---|---|---|---|---|---|
| CHR1 | 5000 | 10000 | CHR1 | 5000 | 10000 | 0.33 |
| CHR1 | 5000 | 10000 | CHR1 | 10000 | 13000 | 0.7 |
| CHR1 | 30000 | 35000 | CHR2 | 5000 | 10000 | 19 |
| CHR1 | 30000 | 35000 | CHR2 | 10000 | 15000 | 23.5 |

$$\begin{bmatrix} 0 & 0 & 0 \\ 0 & 10 & 5 \\ 0 & 0 & 0 \end{bmatrix}$$

row_mask: [0 1 0]
col_mask: [0 1 1]

RECEIVING A CONTACT MATRIX DATA STRUCTURE, THE CONTACT MATRIX DATA STRUCTURE COMPRISING: A HEADER CONTAINING AN INTERVAL OF A CONTACT MATRIX, A LIST OF INTERVAL MULTIPLIERS, A TILE SIZE, A LIST OF CHROMOSOMES WITH A CORRESPONDING IDENTIFIER AND LENGTH, A LIST OF SAMPLE IDENTIFIERS, ZERO OR MORE NAMES OF METHODS OF NORMALIZATION PERFORMED ON THE CONTACT MATRIX TILES; ZERO OR MORE BIN PAYLOAD HAVING AN INTERVAL MULTIPLIER; AT LEAST ONE PARAMETER SET — 1802

BASED ON THE CONTACT MATRIX DATA STRUCTURE, A DESIRED PAIR OF CHROMOSOMES AND A DESIRED INTERVAL MULTIPLIER CORRESPONDING TO A DESIRED INTERVAL OF AN OUTPUT CONTACT MATRIX, GENERATING AN OUTPUT CONTACT MATRIX — 1804

FIG. 18

SYSTEM AND METHOD OF EFFICIENT CODING AND DECODING OF CONTACT MATRICES

PRIORITY CLAIM

The present application is a non-provisional application claiming priority to provisional application No. 63/252,225 filed Oct. 5, 2021, the contents of which are incorporated herein by reference.

FIELD

The present disclosure generally relates to MPEG genomic coding processes and more specifically to an updated contact matrix.

BACKGROUND

Parts 1-5 of the ISO/IEC 23092 (MPEG-G or MPEG genome) standard deal with the representation of genomic information derived from the primary analysis of high-throughput sequencing (HTS) data such as sequencing reads and qualities, and their alignment to a reference genome. The results of primary analysis are usually processed further in order to obtain higher-level information. Such a process of aggregating information deduced from single reads and their alignments to the genome into more complex results is generally known as secondary analysis. In most HTS-based biological studies, the output of secondary analysis is usually represented as different types of annotations associated to one or more genomic intervals on the reference sequences.

BRIEF SUMMARY

In some examples, techniques are described herein for encoding and/or decoding a contact matrix data structure. An example method can include receiving a contact matrix data structure, wherein the contact matrix data structure can include one or more of: a header containing an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payloads and, based on the contact matrix data structure, a desired pair of chromosomes and a desired interval multiplier corresponding to a desired interval of an output contact matrix, generating the output contact matrix.

In another example, a system can include a processor and a computer-readable storage device storing a contact matrix data structure. The contact matrix data structure can include a header containing an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payload.

In another example, a non-transitory computer-readable medium is provided that has stored thereon instructions that, when executed by one or more processors (e.g., implemented in circuitry), cause the one or more processors to: receive a contact matrix data structure, wherein the contact matrix data structure can include one or more of: a header containing an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payloads and, based on the contact matrix data structure, a desired pair of chromosomes and a desired interval multiplier corresponding to a desired interval of an output contact matrix, generate the output contact matrix.

In another example, an apparatus for encoding a contact matrix structure can include a system including a processor and a computer-readable storage device. The computer-readable storage device can store a contact matrix and related information and a program which, when executed by the processor, causes the processor to generate a contact matrix structure according to any of the concepts and syntax structures disclosed below.

Embodiments can include systems and methods for coding a contact matrix. An example method can include coding a contact matrix data structure from a contact matrix, the contact matrix data structure including: a header containing an interval of a contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payloads. The method can include receiving the contact matrix and, based on the contact matrix, generating the contact matrix data structure.

An example encoder can include a system including a processor and a computer-readable storage device storing a contact matrix, related information and program instructions wherein the program instructions, when executed by the processor, cause the processor to perform operations. The operations can include receiving the contact matrix from the computer-readable storage device and, based on the contact matrix, generating a contact matrix structure, wherein the contact matrix structure comprises: a header containing an interval of the contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payloads.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative embodiments of the present application are described in detail below with reference to the following drawing figures:

FIG. 2 illustrates the main contact matrix according to some aspects of this disclosure;

FIG. 3 illustrates a sub-contact matrix for chromosome pairs chr1-chr2 (intra) according to some aspects of this disclosure;

FIG. 4 illustrates a sub-contact matrix for chromosome pairs chr1-chr2 (inter) according to some aspects of this disclosure;

FIG. 7 illustrates additional information "KR" of the main contact matrix according to some aspects of this disclosure;

FIG. 9 illustrates a dense matrix form of chromosome pair chr1-chr2 according to some aspects of this disclosure;

FIG. 12 illustrates a row and column mask according to some aspects of this disclosure;

FIG. 18 illustrates a method embodiment according to some aspects of this disclosure.

DETAILED DESCRIPTION

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the application. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the application as set forth in the appended claims.

Figure 1A:
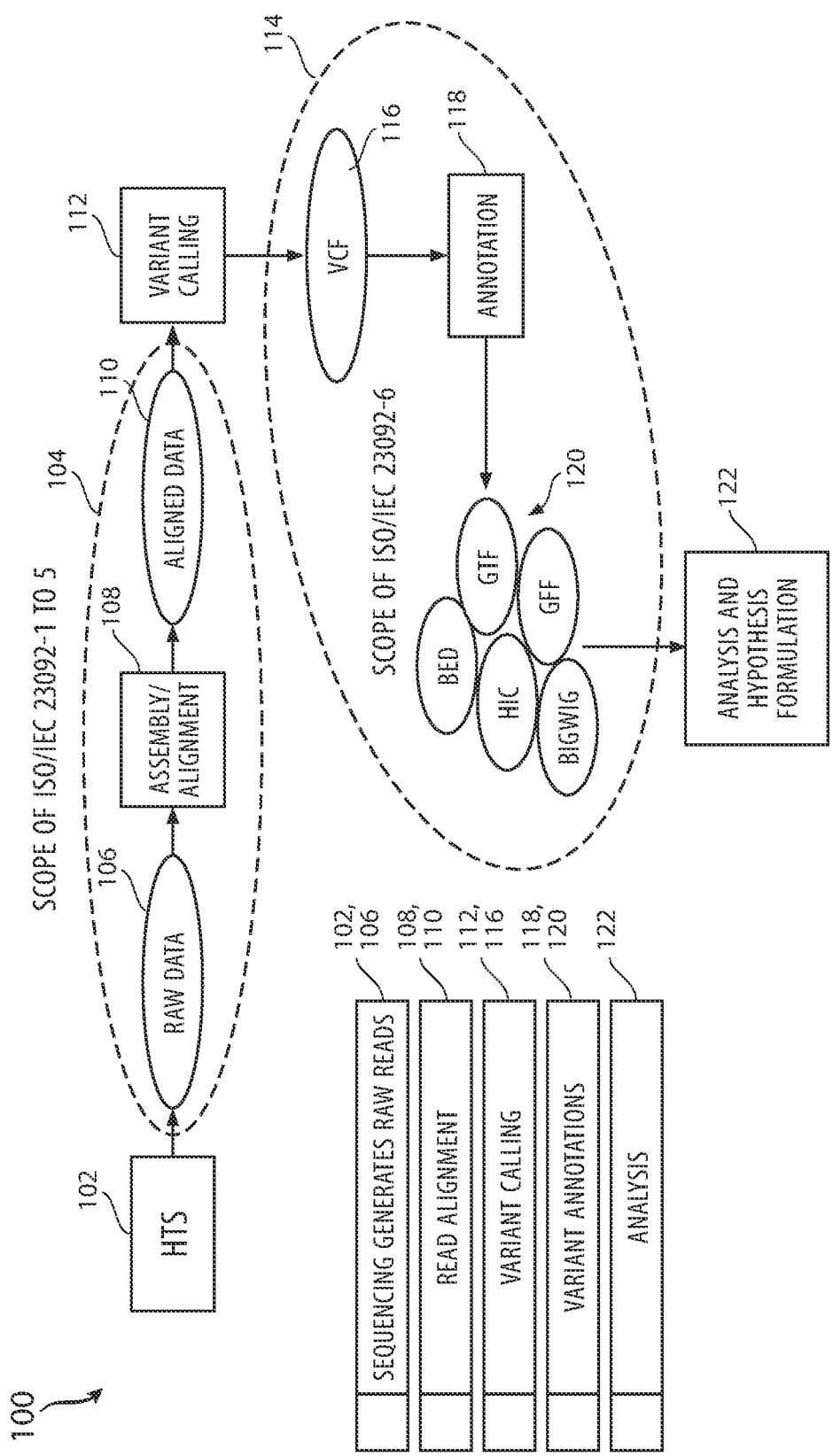
FIG. 1A illustrates a typical pipeline for the primary and secondary analyses of high-throughput sequencing (HTS) data, the file formats involved and the scopes of different parts of the ISO/IEC 23092 standard.

Biological studies typically produce genomic annotation data such as mapping statistics, quantitative browser tracks, variants, genome functional annotations, gene expression data and Hi-C contact matrices. These diverse types of downstream genomic data are currently represented in different formats such as VCF (Variant Call Format—that specifies the format of a text file used in bioinformatics for storing gene sequence variations), BED (Browser Extensible Data—which is a format of a text file format used to store genomic regions as coordinates and associated annotations), WIG (Wiggle format—which is designed for display of dense continuous data such as probability scores, etc.), with loosely defined semantics, leading to issues with interoperability, the need for frequent conversions between formats, difficulty in the visualization of multi-modal data and complicated information exchange. FIG. 1A depicts a typical pipeline 100 for the primary and secondary analyses of HTS data, the file formats involved and the scopes of different parts of the ISO/IEC 23092 standard. The HTS data 102 is provided to a component 104 that receives the raw data 106 and performs an assembly or alignment process 108 to generate aligned data 2110. The sequencing process generates the raw data reads 106. Then a variant calling component 112 generates data which is provided to a component 114 that includes a VCF (variant calling format) 116 which produces variant annotations 118. There can be a variety of ways to process variant annotations such as BED (browser extensible data), GFT (gene transfer format), HiC (hic format), GFF (general feature format or gene finding format) and BigWig (bigwig format) 120 and an output is the analysis and hypothesis formulation 122.

Figure 1B:
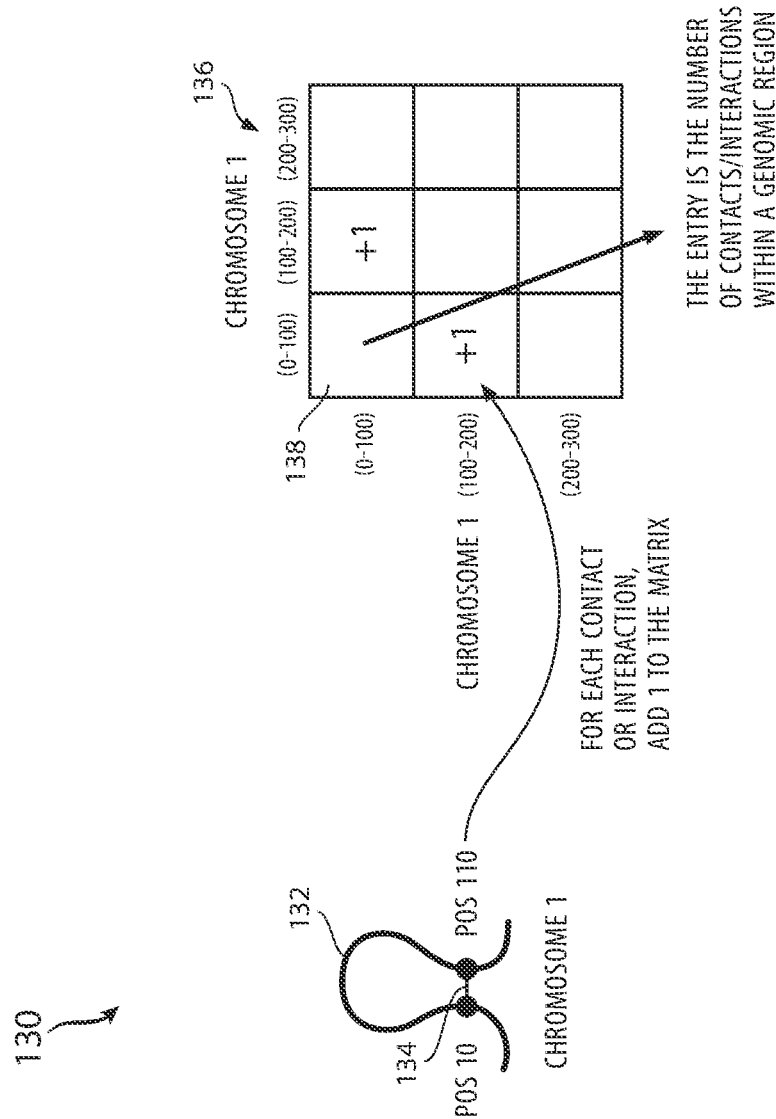
FIG. 1B illustrates an example of a contact matrix.

FIG. 1B illustrates an example of a chromosome 1 132 has a "contact" or an "interaction" 134 between position 10 and position 110. In a table 136, a "1" is added for each contact or interaction depending on the position of the contact. In a particular location 138 in the table 136, the entry is the number of contacts or interactions within a genomic region. In the column 0-100 (feature 138), the contact matrix has an interval or resolution of 100.

The lack of a single format has stifled the work on compression algorithms and has led to the widespread use of general compression algorithms with suboptimum performance. These algorithms do not exploit the fact that the annotation data typically includes multiple fields (attributes) with different statistical characteristics and instead compress them together. Therefore, while these algorithms support efficient random access with respect to genomic position, they do not allow extraction of specific fields without decompressing the whole file.

There have been efforts to produce a unified data format for the efficient representation and compression of diverse genomic annotation data for file storage or data transport. The benefits are manifold: reducing the cost of data storage, improving the speed of random data access and processing, providing support for data security and privacy in selective genomic regions, and creating linkages across different types of genomic annotation and sequencing data. The ultimate goal is to enable the secured and seamless sharing, processing and analysis of multi-modal genomic data in order to reduce the burden of data manipulation and management, so scientists can focus on biological interpretation and discovery.

This disclosure introduces additional novel features related to a unified data format for the representation of genomic annotation data for file storage and transport. The data structure can be called a contact matrix codec (CMC) data structure. The new data structure can include a header containing one or more of a bin interval of a contact matrix tile, a list of chromosomes with a corresponding name and length, sample names and a name of a method of normalization performed on the contact matrix tile; a bin payload having an interval multiplier; a parameter set; and a matrix tile payload. Embodiments which can be claimed based on this disclosure include codec (coder/decoder) systems for either coding or decoding of data structures associated with a contact matrix, methods of coding and/or decoding and/or computer-readable media or devices storing computer instructions which cause a computer processor to perform coding and/or decoding operations.

Next is discussed various methods for coding the contact matrix after which the disclosure will introduce in more detail the new CMC data structure.

The following discussion relates to technology for the coding of a (diagonally dominant) integer matrix especially a contact matrix having a data structure as disclosed herein.

The value "0" can be an indicator for a value not to be processed in the contact matrix. The distinction between "0" as a regular number and "0" as an indicator is clear in the specification. The actual value of the indicator might be set to any pre-determined value and does not have to be "0" per se.

A contact matrix can be represented in a sparse matrix form which consists of the following columns:

[chrom1 start1 end1 chrom2 start2 end2 count]

The count is the number of contacts within certain genomic region described by start1, end1, start2 and end2. The size of genomic region is called a resolution and a contact matrix has a uniform resolution size. Therefore, this information can be computed by subtracting the end with the start.

If any matrix normalization or balancing is done, additional information necessary for the normalization is stored in the additional columns after the count column. One example approach, which is not limiting to this exact approach, is to user Knight-Ruiz Matrix Balancing (KR):

[chrom1 start1 end1 chrom2 start2 end2 count KR]

FIG. 2 illustrates a main contact matrix structure 200 with the resolution of 5000 represented in a sparse matrix form. The contact matrix that contains all possible chromosome pairs (chrom1 and chrom2) is called the main contact matrix.

For the coding process, the main contact matrix 200 is split into multiple sub-contact matrices based on its chromosome pair (chrom1 and chrom2), resulting in the sub-contact matrix C that contains only one unique value for chrom1 and chrom2 (chr1 for chrom1 and chr1 for chrom2 in FIG. 3).

The sub-contact matrix can be classified into 2 different classes depending on the value of chrom1 and chrom2:

A. Intra sub-contact matrix: When chrom1 is equal to chrom2

B. Inter sub-contact matrix: When chrom1 is different from chrom2

FIG. 3 shows an example of the sub-contact matrices 300 originated from the main contact matrix 200 for chromosome pairs chr1-chr2 (intra). FIG. 4 illustrates the sub-contact matrix 400 for chromosome pairs chr1-chr2 (inter). See FIG. 13 for the example of different types of matrices such as the intra and the inter types.

The coding process can include one or more steps related to transforming from one matrix representation to another, splitting the contact matrix into sub-matrices called contact matrix tiles and performing encoding of the resulting contract matrix tiles. An encoder can include a processor and programming code that causes the processor to perform the operations. Other optional steps can be included as well. An example coding process of a sub-contact matrix can include one or more of the following steps:

1. Transformation from sparse matrix representation to dense matrix representation.
2. Optionally, creating binary masks to mark the rows or columns which have only zero values.
3. Splitting the contact matrix into sub-matrices called contact matrix tile.
4. Optionally, perform diagonal transformation on each contact matrix tile.
5. Optionally, binarize the rows or columns of the data.
6. Entropy coding.

Figure 5:
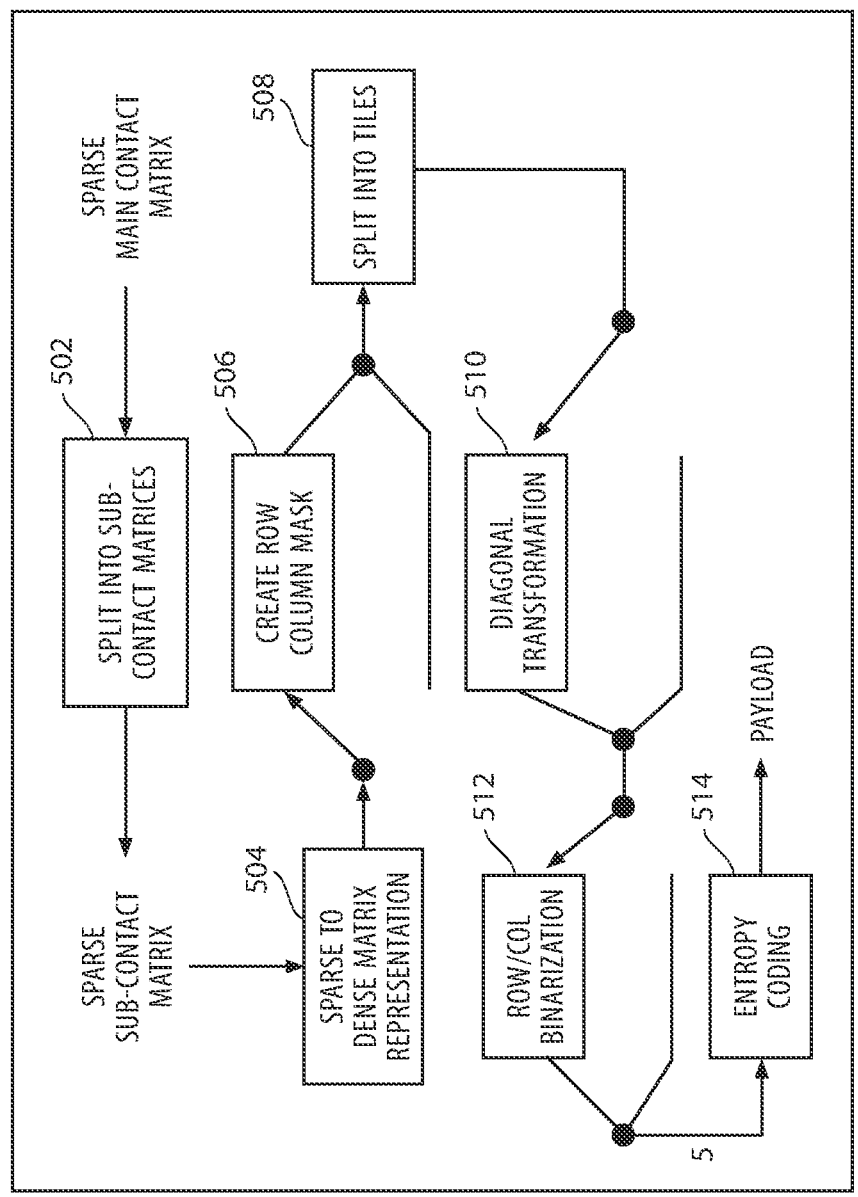
FIG. 5 illustrates the coding process for a sub-contact matrix according to some aspects of this disclosure.

If the input data is in dense matrix form, the first transformation step can be skipped. FIG. 5 illustrates the coding process 500 of the sub-contact matrix 400. Optional transformations are switched on. The steps include splitting the sparse main contact matrix into sub-contact matrices (502), converting from a sparse to dense matrix representation (504), creating both row and column masks (506), splitting the matrix into tiles (508), performing a diagonal transformation (510), performing a row/column binarization (512) and performing an encoding such as for example an entropy encoding (514) to produce the payload. Each of these steps can be also represented as modules or components that perform the steps as part of an encoder or codec.

Figure 6:
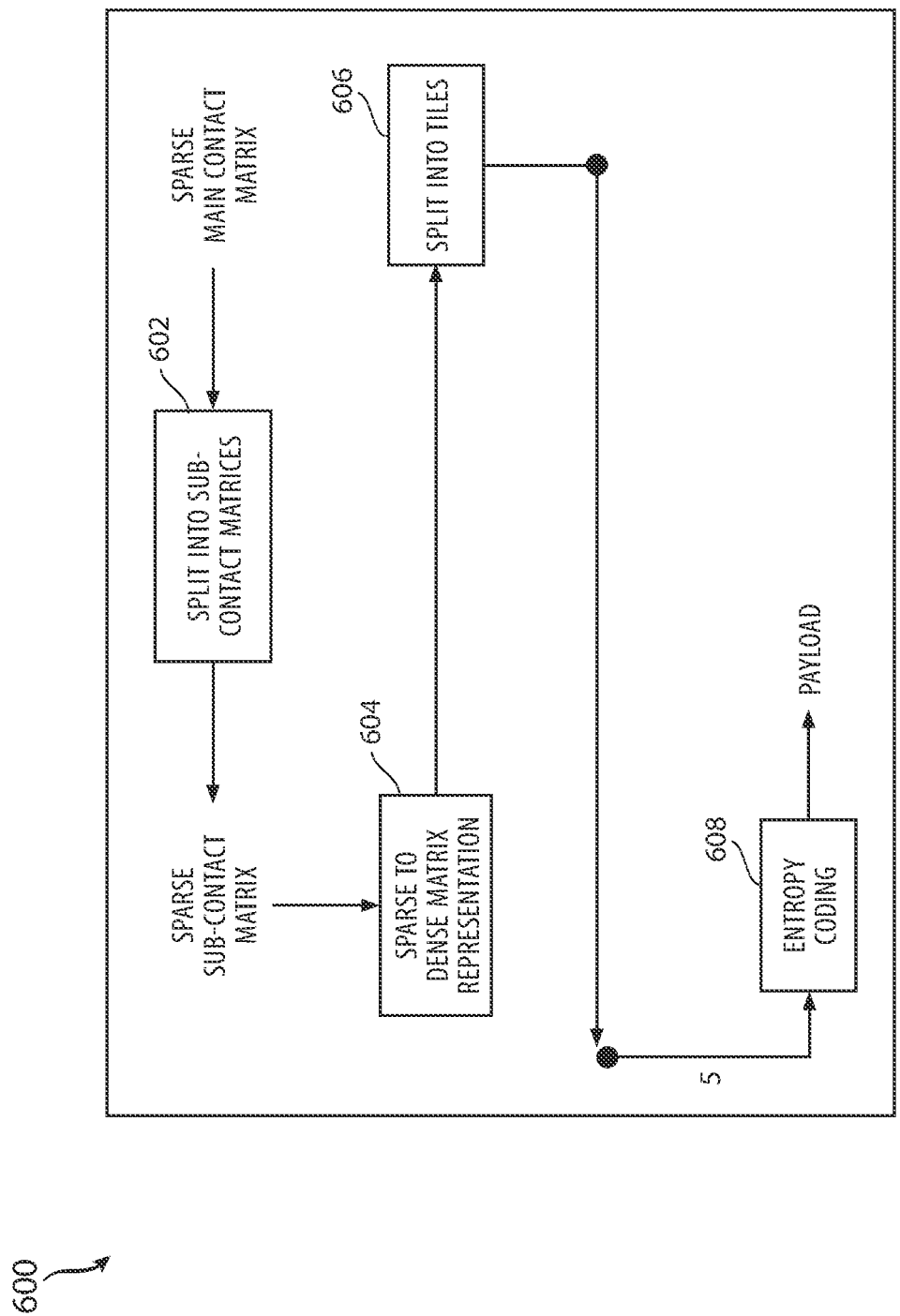
FIG. 6 illustrates a coding process of the additional information of a sub-contact matrix according to some aspects of this disclosure.

FIG. 6 illustrates a coding process 600 of the additional information (such as a normalized matrix) of a sub-contact matrix. The process can include splitting sparse main contact matrix into sub-contact matrices (602), converting from a sparse to a dense matrix representation (604), splitting the matrix into tiles (606) and performing coding (608) to produce the payload. Each of these steps can be also represented as modules or components that perform the steps as part of an encoder or codec.

For the additional information mentioned before such as "KR", it is transformed in similar fashion to the one done for the main contact matrix where the resulting matrix or tile before entropy coding is a matrix with floating-point values. The process is depicted in FIG. 6.

FIG. 7 illustrates the additional information "KR" of the main contact matrix. This information can be stored using the same transformation or the transformation according to FIG. 6. In one example, the additional information can be called a precomputed normalized contact matrix.

Next is discussed the transformation to a dense matrix representation as illustrated in step (504) of FIG. 5 or step (604) of FIG. 6. To transform a sub-contact matrix from sparse matrix representation to a dense matrix representation, three values must be computed or transmitted: interval, chr1_max_pos and chr2_max_pos.

Assuming that each column is a vector, resolution of chrom1 can be computed as follows:

$$resolution_{chr1} = \max_{i=0, i<n} (end1_i - start1_i)$$

where n is the number of rows of the sub-contact matrix, $end1_i$ is the value of end1 at row i and $start1_i$ is the value of start1 at the row i. To compute the resolution of chrom2, $end1_i$ can be substituted by $end2_i$ and at the same time the $start1_i$ is substituted by $start2_i$.

Both chrom1 and chrom2 have the same resolution, therefore computation from either one of it is sufficient to compute the resolution of the sub-contact matrix of a given chromosome pair.

Using the example depicted in FIG. 2 to FIG. 4, the computed resolution of both sub-contact matrices is 5000.

The maximum positions chr1_max_pos and chr2_max_pos are retrieved from end1 and end2 respectively.

$$chr1\_max\_pos = \max_{i=0,i<n}(end1_i)$$

$$chr2\_max\_pos = \max_{i=0,i<n}(end2_i)$$

After all of the three necessary or helpful information are computed, the values of row_idx and col_idx vectors can be computed using the following formula:

row_idx$_i$=start1$_i$/resolution col_idx$_i$=start2$_i$/resolution

Figure 8:
FIG. 8 illustrates an intermediate result of a sub-contact matrix of chromosome pair chr1-chr2 according to some aspects of this disclosure.

Through this process a new sub-contact matrix is obtained for the respective chromosome pair. Using the example depicted in FIG. 2, the resulting sub-contact matrix 800 is shown in FIG. 8. This shows the intermediate result of the sub-contact matrix of chromosome pair chr1-chr2. FIG. 2 shows the main contact matrix. FIG. 3 illustrates the resulting sub-contact matrix for chr1-chr pair from FIG. 2 and FIG. 8 shows the result.

FIG. 8 illustrates a sparse matrix form of the cub-contact matrix of chromosome pair chr1-chr1. Based on this information, transformation of the sparse matrix to dense matrix (initialized to 0) can be done using row_idx, col_idx and count. Information of chrom1 and chrom2 can be represented by using one value each as there is only one unique value for each respective column.

Figure 9:
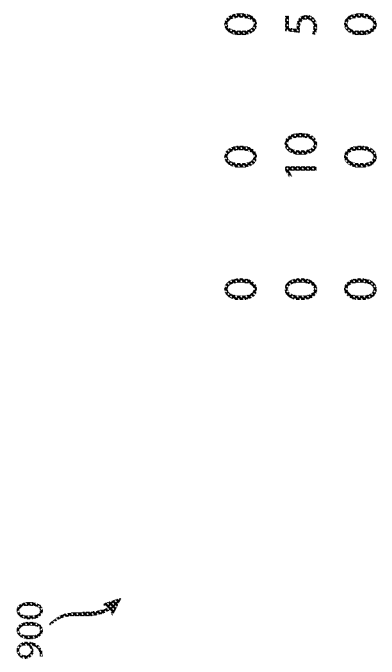

FIG. 9 illustrates a dense matrix form 900 of the sub-contact matrix of chromosome pair chr1-chr1. Because intra sub-contact matrix is implicitly a square matrix, extra rows with a pre-determined value are appended at the end so that the shape is square.

Figure 10:
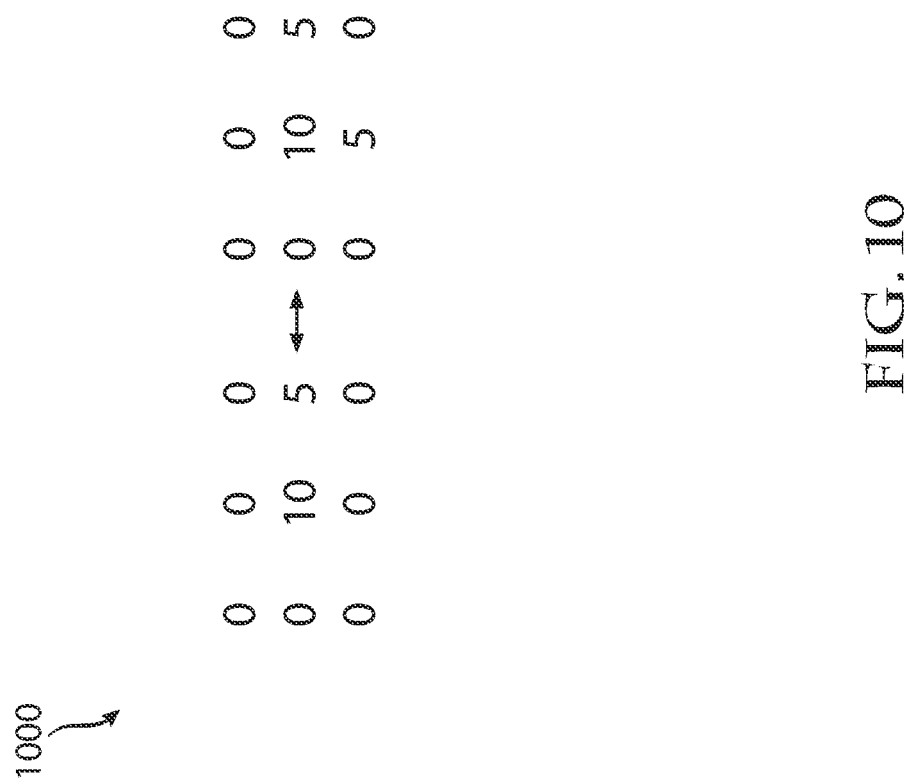
FIG. 10 illustrates a dense matrix for an intra class with and without a zero lower triangle according to some aspects of this disclosure.

The resulting dense matrix of this process for an intra class is a square (symmetrical) matrix and a matrix for an inter class sub-contact matrix. For the intra-case, the dense (sub-) contact matrices are square and symmetric (implicitly). However, only the upper triangle and the main diagonal of the matrix are relevant. Therefore, for the symmetrical matrix (intra class), the lower triangle of the matrix can be set to zero (or implicitly zero). The lower triangle part can be set to zero or predefined value due to a symmetrical property. FIG. 10 illustrates a dense matrix for the intra class with and without a zero lower triangle. The number of rows of the sub-contact matrix is called nrows and the number of columns of the sub-contact matrix is called ncols.

Note that it is not necessary to completely transform the sparse representation to dense representation. The intermediate result depicted in FIG. 8 is sufficient as input for the remaining transformations described in FIG. 5 and FIG. 6. For the additional information, such as column "KR", will not be transformed into dense matrix form. An example can be seen in FIG. 11 of the result 1100 of dense matrix transformation of additional information for sub-contact matrix of chromosome pair chr1-chr2.

With additional information, the rows must be sorted by row_idx and col_idx. In one aspect, the order of the sorting matters.

Next the concept of creating binary masks is discussed. In this optional process, the binary masks for both rows and columns are computed. The purpose is to reduce the size of sub-contact matrix (or tile) by marking the rows and columns containing zero values or indicators or pre-determined values which are removed in the next step. The row and column binary masks represent whether the row or the column contain a non-pre-determined value or not. As an example: 1 or true for non-zero and 0 or false for zero row or column.

Using the example in FIG. 9, FIG. 12 shows a row and column mask 1200. The first column and the first row contain only zeros. Thus, the first value of the row and column binary mask is zero or false. The last row contains only zero but due to the property of symmetrical matrix (see FIG. 10), the last row is non-zero (see FIG. 10).

For intra sub-contact matrix, it is sufficient to transmit the col_mask only due to the symmetrical property (see FIG. 10), where for inter case both row_mask and col_mask must be transmitted.

Next the concept of splitting the matrix into tiles is discussed. In this process, the sub-contact matrix is further split into square matrices called contact matrix tiles or tile with the size of tile_size.

Figure 13:
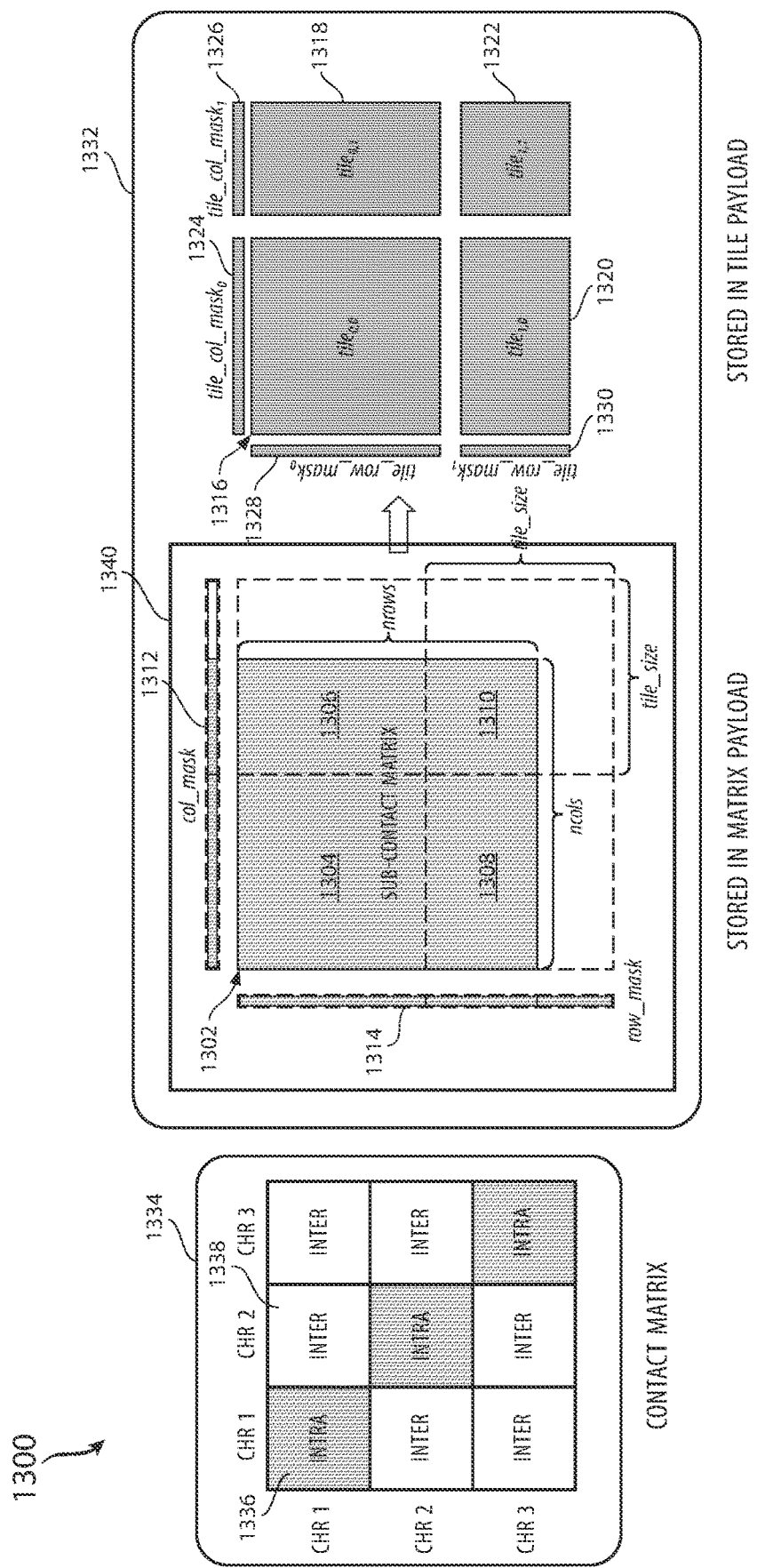
FIG. 13 illustrates splitting a sub-contact matrix into tiles according to some aspects of this disclosure.

FIG. 13 illustrates the process 1300 of splitting the matrix 1334 into different sub-contact matrices 1334, 1336. The "intra" types of a contact matrix 1336 relates to a pair of same chromosomes and the inter 1338 type of contact matrix relates to a pair of different chromosomes. The sub-contact matrix is further split into tiles in the process 1332. The goal of this transformation is to maximize either the coding efficiency or minimize the access time. It can also balance the trade-off between these two metrics. For a faster access time, the tile_size can be set to a lower value and to maximize the coding efficiency, the tile_size can be set to a higher value. For example, for the highest or for an acceptable efficiency, the number of resulting tiles would be 1. The right side of FIG. 13 shows the sub-contact matrix 1340. Stored in a matrix payload (e.g., see matrix payload 1508 of FIG. 15), is the sub-contact matrix 1302 and associated masks 1312, 1314. A tile 1316 can be stored in the tile payload 1510 shown in FIG. 15.

Depending on the relative position of the tile to the sub-contact matrix, the contact matrix tile would have a rectangular shape 1318, 1320 instead of square shape 1316, 1322 as depicted in FIG. 13.

The number of tiles in row and column direction can be computed as follows:

ntiles_in_row_dir=Ceil(nrows/tile_size)

ntiles_in_col_dir=Ceil(ncols/tile_size)

If the row_mask 1314 and col_mask 1312 are created in the previous step, both row_mask and col_mask are split into tile_size length masks called tile_row_mask$_i$ 1328, 1330 and tile_col_mask$_j$ 1324, 1326 respectively.

Each of the tile is indexed by its relative position in the sub-contact matrix using the notation tile$_{i,j}$ with 0≤i<ntiles_in_row_dir and 0≤j<ntiles_in_col_dir.

Each tile is then sliced based on its respective row_mask 1314 and col_mask 1312. If both row_mask and col_mask are unavailable due to previous step being skipped, this slicing process will also be skipped.

If tile_size is equal to 0, then the size of the tile is equal to the size of the sub-contact matrix.

Figure 11:
FIG. 11 illustrates a result of dense matrix-transformation of additional information for sub-contact matrix of chromosome pair chr1-chr2 according to some aspects of this disclosure.

For the additional information (i.e., "KR" in FIG. 11), the table in FIG. 11 is split into multiple tables, represent each tile. Given the example it becomes:

| row_idx | col_idx | KR |
|---------|---------|------|
| 1 | 1 | 0.33 |

This represents the tile 0 of the sub-contact matrix of chromosome pair chr1-chr1.

| row_idx | col_idx | KR |
|---------|---------|------|
| 1 | 2 | 0.7 |

The above represents tile 1 of the sub-contact matrix of chromosome pair chr1-chr1. After that, only the columns of the additional information "KR" are transmitted and encoded by the entropy coder.

Next is discussed the diagonal transformation (feature 510 from FIG. 5). In most of cases, especially for the intra sub-contact matrix, the matrix is diagonal dominant. This means that the values in the diagonal require more bits compared to the other elements of the matrix due to a greater magnitude. Decomposing the value into multiple bit planes or directly using the row/col binarization is inefficient because each row requires bits proportional to the bits required by the value in the diagonal. Given the following example:

$$\begin{bmatrix} 127 & 2 & 3 \\ 3 & 125 & 7 \\ 1 & 3 & 120 \end{bmatrix} \rightarrow \begin{bmatrix} 8 \text{ bits} \\ 8 \text{ bits} \\ 8 \text{ bits} \end{bmatrix}$$

where each row requires 8 bits to represent the values. By diagonal transform the matrix:

$$\begin{bmatrix} 127 & 125 & 120 \\ 2 & 7 & 3 \\ 3 & 1 & 3 \end{bmatrix} \rightarrow \begin{bmatrix} 8 \text{ bits} \\ 4 \text{ bits} \\ 2 \text{ bits} \end{bmatrix}$$

where the number of bits required to represent the matrix is greatly reduced.

Figure 14:
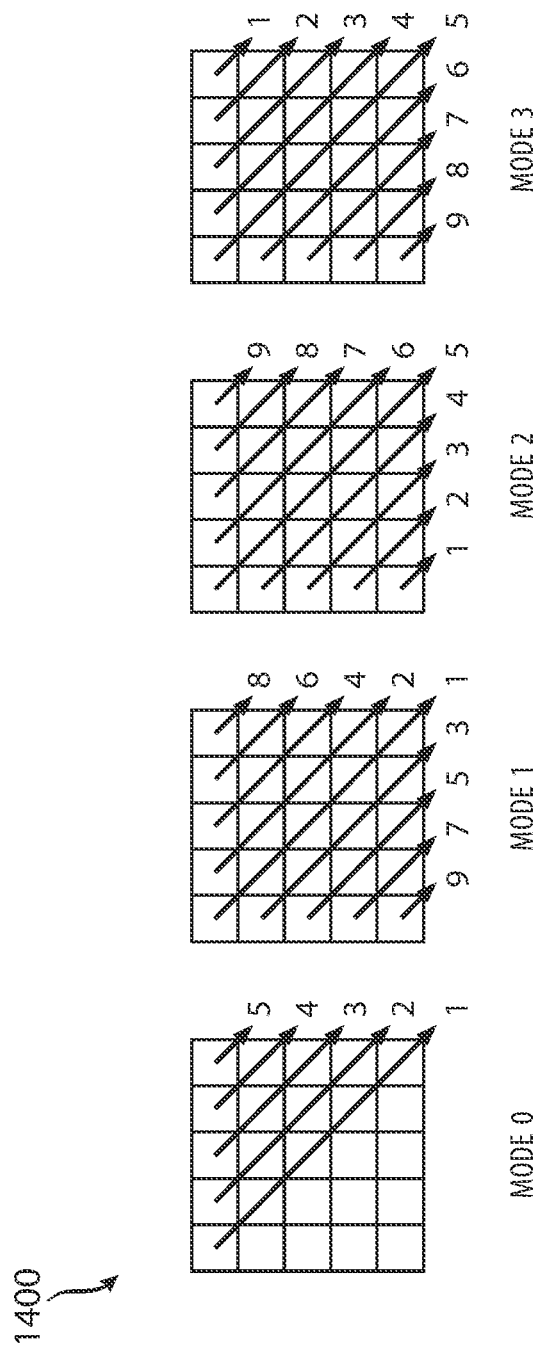
FIG. 14 illustrates diagonal transformation modes according to some aspects of this disclosure.

In total there are 4 modes for diagonal transformation proposed as shown in FIG. 14. As the name implies, the values of the original matrix or tile in the diagonal direction are placed in the transformed tile starting from the first row and column, then continuing in the column direction. The processed diagonal depends on the mode.

Given a tile (i.e., an original tile before transformation) as follows:

$$\begin{bmatrix} 0 & 1 & 2 & 3 & 4 \\ 5 & 6 & 7 & 8 & 9 \\ 10 & 11 & 12 & 13 & 14 \\ 15 & 16 & 17 & 18 & 19 \\ 20 & 21 & 22 & 23 & 24 \end{bmatrix}$$

The transformed tile using mode 0 becomes:

$$\begin{bmatrix} 0 & 6 & 12 & 18 & 24 \\ 1 & 7 & 13 & 19 & 2 \\ 8 & 14 & 3 & 9 & 4 \\ X & X & X & X & X \\ X & X & X & X & X \end{bmatrix} \rightarrow \begin{bmatrix} 0 & 6 & 12 & 18 & 24 \\ 1 & 7 & 13 & 19 & 2 \\ 8 & 14 & 3 & 9 & 4 \end{bmatrix}$$

The mode 0 may only be used for a (implicitly symmetrical) matrix or tile and the diagonals processed are the main diagonal and the upper triangle. The lower triangle does not need to be processed as it contains only zeros, depicted with 'X'. The rows containing only zeros in the transformed tile are then removed. As an example of a transformation of an intra-class tile using mode 0:

$$\begin{bmatrix} 255 & 10 & 5 & 3 & 1 \\ 0 & 255 & 10 & 5 & 3 \\ 0 & 0 & 255 & 10 & 5 \\ 0 & 0 & 0 & 255 & 10 \\ 0 & 0 & 0 & 0 & 255 \end{bmatrix} \rightarrow \begin{bmatrix} 255 & 255 & 255 & 255 & 255 \\ 10 & 10 & 10 & 10 & 5 \\ 5 & 5 & 3 & 3 & 1 \\ X & X & X & X & X \\ X & X & X & X & X \end{bmatrix}$$

$$\rightarrow \begin{bmatrix} 255 & 255 & 255 & 255 & 255 \\ 10 & 10 & 10 & 10 & 5 \\ 5 & 5 & 3 & 3 & 1 \end{bmatrix}$$

For mode 1, after the main diagonal is processed, the diagonals of lower and upper triangles are processed in an alternating fashion. The following shows a transformation of a tile using mode 1.

$$\begin{bmatrix} 0 & 6 & 12 & 18 & 24 \\ 1 & 7 & 13 & 19 & 5 \\ 11 & 17 & 23 & 2 & 8 \\ 14 & 10 & 16 & 22 & 3 \\ 9 & 15 & 21 & 4 & 20 \end{bmatrix}$$

Unlike mode 0 and 1, both mode 2 and 3 do not start from the main diagonal. Mode 2 starts from the diagonal corresponding to the last row and the diagonal corresponding to the last column for mode 3. The following is a transformed tile using mode 2.

$$\begin{bmatrix} 20 & 15 & 21 & 10 & 16 \\ 22 & 5 & 11 & 17 & 23 \\ 0 & 6 & 12 & 18 & 24 \\ 1 & 7 & 13 & 19 & 2 \\ 8 & 14 & 3 & 9 & 4 \end{bmatrix}$$

The following is a transformed tile using mode 3.

$$\begin{bmatrix} 4 & 3 & 9 & 2 & 8 \\ 14 & 1 & 7 & 13 & 19 \\ 0 & 6 & 12 & 18 & 24 \\ 5 & 11 & 17 & 23 & 10 \\ 16 & 22 & 15 & 21 & 20 \end{bmatrix}$$

Additional modes for transforming a tile are possible. The proposed modes (FIG. 14) may be replaced by others.

Next is discussed the row/column binarization process (feature 512 from FIG. 5). In this optional process the values of the matrix or tile A are decomposed row- or column-wise to its binary representation. This yields the binary matrix or tile B where $b_{i,j}$ is the element of it.

The binarization comprises the following steps:
1. Select the direction of binarization, either row direction or column direction. The direction cannot be changed during the process.
2. For each row i or row j the maximum value or of the corresponding row $a_i^{max}$ or column $a_j^{max}$ is determined. The following is the computation of a maximum value $a^{max}$.

$$a_i^{max} = \max_{\forall j}(a_{i,j})$$

$$a_j^{max} = \max_{\forall i}(a_{i,j})$$

3. The number of binary rows or columns resulting from the current row or column is equal to the bit length q required to represent $a_i^{max}$ or $a_j^{max}$ and can be computed using formula, which is a computation of a bit length q:

$$q_i = \lceil \log_2(a_i^{max}+1) \rceil$$

$$q_j = \lceil \log_2(a_j^{max}+1) \rceil$$

4. The k-th binary row or column contains the k-th bit of the original row or column. After an original row or column is decomposed, the binary rows or columns are concatenated in row or column direction, respectively. One bit is added to the beginning of row or column to signal the last row or column generated given the original row or column. 1 or true means the last bit, otherwise 0 or false.

Below is an example for this process:

$$A = \begin{bmatrix} 1 & 2 & 3 \\ 4 & 5 & 6 \end{bmatrix}$$

Assume the binarization is done in row direction. For each row, $a_i^{max}$ is computed:

$$a_0^{max}=3, a_1^{max}=6$$

Given the maximum value of each row, the bit length required to store information can be computed as q values:

$$q_0=2, q_1=3$$

For each row, the values are decomposed to binary rows:

$$[1\ 2\ 3] \rightarrow \begin{bmatrix} 1 & 0 & 1 \\ 0 & 1 & 1 \end{bmatrix}$$

$$[4\ 5\ 6] \rightarrow \begin{bmatrix} 0 & 1 & 0 \\ 0 & 0 & 1 \\ 1 & 1 & 1 \end{bmatrix}$$

Then one column is added on the left side for the marker of the last bit:

$$\begin{bmatrix} 0 & 1 & 0 & 1 \\ 1 & 0 & 1 & 1 \end{bmatrix}$$

$$\begin{bmatrix} 0 & 0 & 1 & 0 \\ 0 & 0 & 0 & 1 \\ 1 & 1 & 1 & 1 \end{bmatrix}$$

Last, the binary rows are concatenated in the selected direction to produce a binary matrix:

$$B = \begin{bmatrix} 0 & 1 & 0 & 1 \\ 1 & 0 & 1 & 1 \\ 0 & 0 & 1 & 0 \\ 0 & 0 & 0 & 1 \\ 1 & 1 & 1 & 1 \end{bmatrix}$$

Next the coding process (such as entropy coding) as shown in feature 514 of FIG. 5. In the last step of the coding process, integer or binary matrix (depending on which transformations are activated) is then encoded using an entropy coder. Both context-based or predictive based codec can be used in this step as long as the codec supports integer or binary values.

Figure 15:
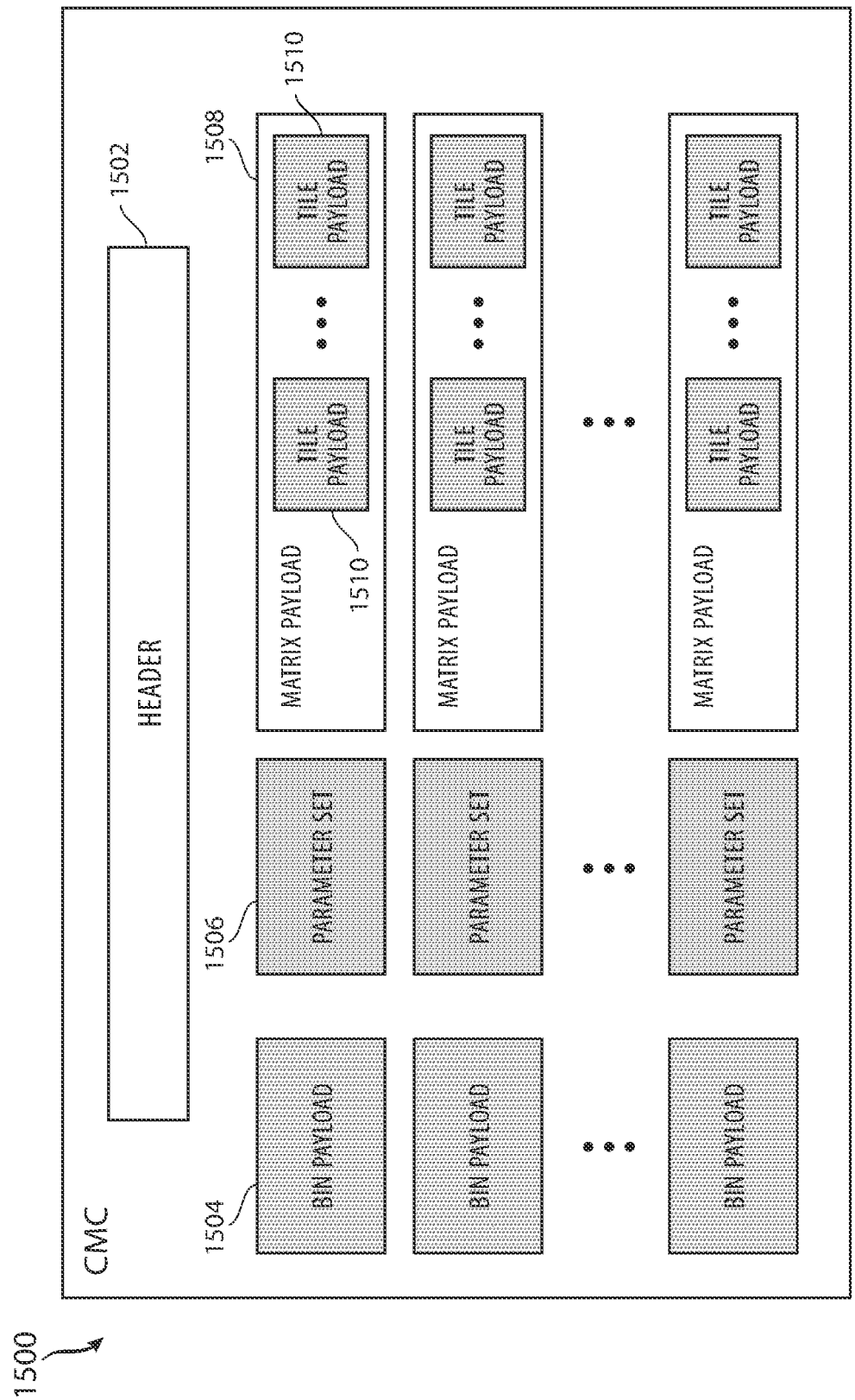
FIG. 15 illustrates an extended structure of the contact matrix according to some aspects of this disclosure.

Next is discussed a new syntax and semantic structure for the contact matrix 1500 as shown in FIG. 15.

The extended structure 1500 now contains new elements such as contact matrix header 1502 and zero or more bin payload 1504. The header 1502 can contain information such as the bin interval of the contact matrix tiles, the list of chromosomes with its corresponding identifier and length, the sample identifiers, and the name of methods of the normalization done to the contact matrix tile. A normalization method could be used for on-the-fly application and/or for a precomputed normalized method. The bin payload 1504 contains an interval multiplier. This is useful in the case of multi-interval and the weights correspond to the higher interval. The weights for each on-the-fly normalization method are also stored in the bin payload. This is done as the weights do not require much space and therefore no compression is necessary. The contact matrix data structure can include one or more bin payloads 1504 which can depend on the number of on-the-fly normalizations.

Additionally, this disclosure uses the term interval instead of resolution to avoid confusion. The reason is higher resolution means better details yet for a contact matrix it becomes less detailed. The extended contact matrix 1500 also includes one or more parameter set 1506, one or more matrix payload 1508 which can include one or more tile payload 1510 for each matrix payload 1508. For every matrix payload 1508, there is an associated parameter set 1506. Additionally, there can be normalized tile payloads 1510 based on the number of precomputed normalized tile.

The matrix payload can be represented by the sub-contact matrix shown on the right side of FIG. 13.

The contact matrix 1500 contains not only the number of contacts within a certain genomic region, which is called contact, but also the normalized value of this contact. The idea of the contact matrix normalization is to iteratively correct the matrix. It transforms a symmetric and non-negative contact matrix A to a doubly stochastic matrix T (flat and equal row and column sum) as described in [1]. Each element of T can be decomposed such as:

$$T_{i,j} = \frac{A_{i,j}}{b_i b_j} = w_i w_j A_{i,j} \quad (1)$$

$$T = DAD \quad (2)$$

where weight $w_i$ and $w_j$ are the entries of the main diagonal of weight matrix D at index i and j respectively. Assuming that division operation is desired, the weight $w_i$ at index i can be stored in a form of $b_i$ which can be computed as follows $$b_i = \frac{1}{w_i} \quad (3)$$

By storing the weights (either b or w), instead of the normalized matrix T, we induce little storage cost as the number or row and columns of the matrix A or T is square root of the number of entries of both matrices. Furthermore, the state-of-the-art transformation and compression pipelines proposed in the document M56622 (Method for the Coding of Contact Matrix, Yeremia Gunawan Adhisantoso and Jörn Ostermann, ISO/IEC JTC 1/SC 29/WG 8, April 2021, incorporated herein by reference) is suitable for integer matrix, which is the original matrix A. If a precomputed normalized contact matrix is required, the normalized matrix T can be stored as specified in the document M56622.

Another extension introduced in this document is multi-interval. In the document M56622, each contact matrix and its corresponding contact matrix tiles correspond to a specific interval. This results in a higher storage cost. Additionally, the contact matrix with larger intervals can be computed from the smaller interval contact matrix given:

interval_high=interval_multiplier*interval_low where interval_multiplier is a positive integer and a factor of tile_size. By limiting interval_multiplier to be a factor of tile_size, the data required to compute each tile of the contact matrix of with higher interval comes from the same payload. Therefore, this simplifies the decoding process.

Figure 16:
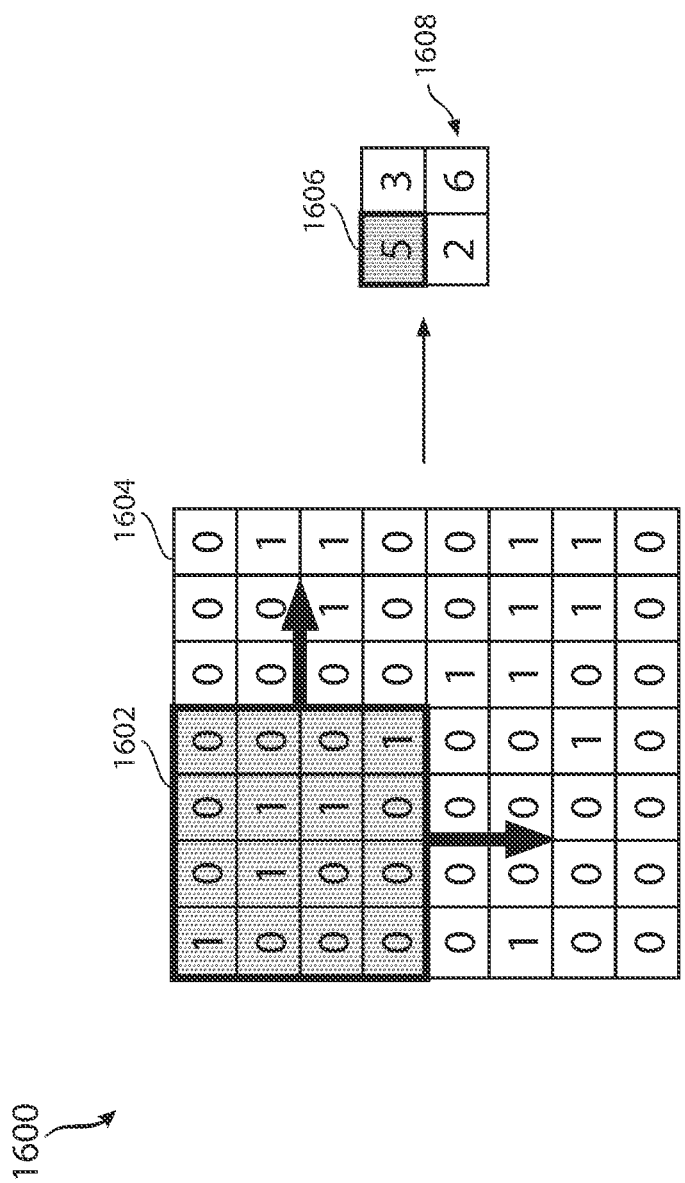
FIG. 16 illustrates a computation of a higher interval contact matrix with an interval multiplier equal to 4 according to some aspects of this disclosure.
Figure 17:
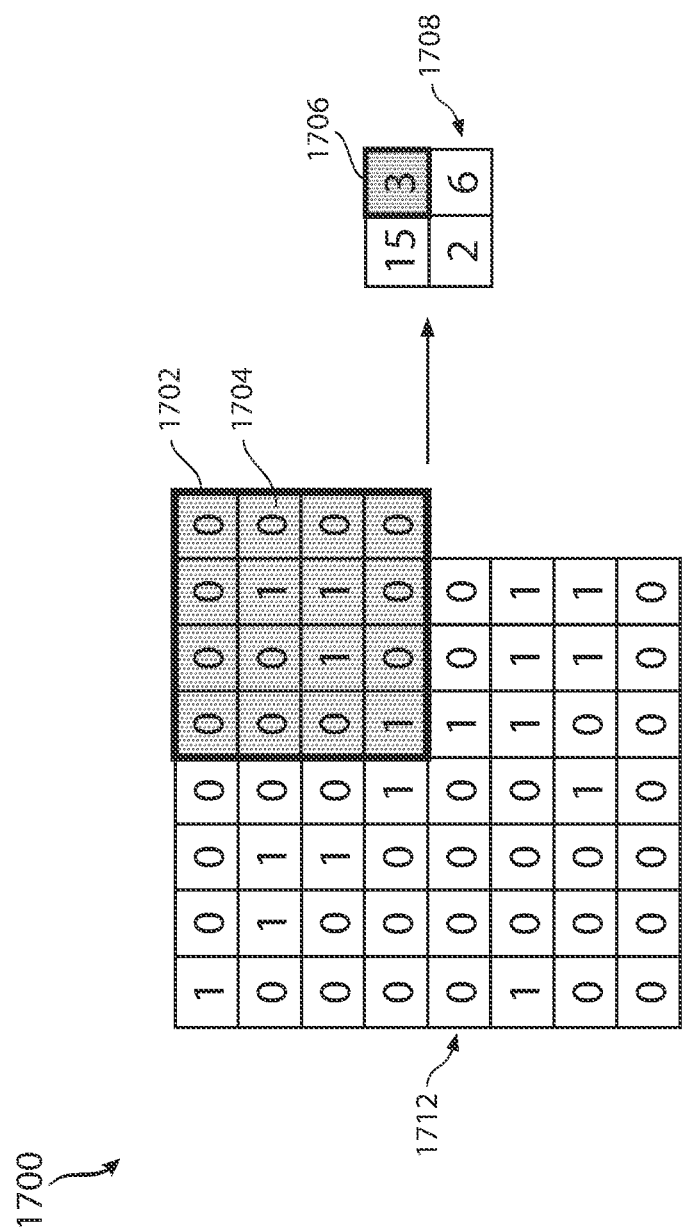
FIG. 17 illustrates a zero padding method according to some aspects of this disclosure.

FIG. 16 illustrates a computation 1600 of a higher interval contact matrix with an interval multiplier equal to 4. FIGS. 16 and 17 show how the perform a computation of a contact matrix/tile with higher interval/low resolution from a contact matrix with low interval or higher resolution.

To compute one entry of contact matrix (tile) with higher interval 1606, a summation of all entries within one window 1602 (2-dimensional convolution operation) with size of interval_multiplier is applied. The window size (i.e., a number of columns in the window 1602 for example) can be a factor of a tile size. The operation starts from the top-left side, then the window 1602 is moved in row or column direction to compute the neighboring entries. The weights (either b or w) of the corresponding high interval contact matrix needs to be stored to compute the normalized contact matrix. As shown in FIG. 16, the number of "1" values in the window 1602 is 5, which value is then stored 1606. A similar approach is used to obtain the other values 3, 2, 6 (1608).

As an example, assume that there is a contact matrix tile 1604 with tile_size of 8 and interval of 100 as depicted in FIG. 16. To compute a contact matrix (tile) 1608 with interval of 400, a convolution operation is done to the contact matrix tile. Window size and interval_multiplier have the same value which is 4. All entries within the window 1602 are summed, resulting in the new entry (5 as feature 1606) of the higher interval contact matrix tile. To compute the neighboring entries, the window is moved to the left and bottom direction with step size or stride equals to window size. Therefore, the windows will not be overlapping.

Following the operation in FIG. 16 is the next step shown in FIG. 17 in which the window 1602 is moved to the right with a step size equal to the window size. The moved window is represented as window 1702. FIG. 17 illustrates a zero padding method 1700 in which as the window 1702 is moved to the right from its original position (from window 1602 shown in FIG. 16), only the main boxes are from the tile 1712 summed by padding zero values 1704 on the right side. Originally, there were no values in location of the zero values 1704. The system either does not sum the values in this region or can pad the region with zeros and then sum the values up 1706. As can be seen, in window 1702 there are three "1" values and thus the value "3" 1706 is used in the higher interval contact matrix 1708.

In the case where the number of entries in either row or column direction is less than the window size, either zero padding or no operation method is applied as depicted in FIG. 17. With no operation method, the summation will be done only on the gray boxes within the window without appending zeros on the right side.

In the following sections we describe the decoding of contact matrices in detail when supporting the described features. Given the decoding description the encoding of a contact matrix can be derived given the text of this invention.

Next is described the syntax and semantic of each structure of the extended CMC. An example of the general syntax of the extended CMC header 1502 as shown in FIG. 15 is provided next:

| Syntax | Type |
|---|---|
| cmc_header( ){ | |
|   dataset_id | u(16) |
|   num_samples | u(8) |
|   for (i=0; i<num_samples;i++){ | |
|     samples_id[i] | u(8) |
|     samples_name[i] | st(v) |
|   } | |
|   num_chrs | u(8) |
|   for (i=0 i<num_chr; i++) | |
|     chrs_id[i] | u(8) |
|     chrs_name[i] | st(v) |
|     chrs_length[i] | u(64) |
|   } | |
|   interval # (replacing resolution) | u(32) |
|   tile_size | u(32) |
|   num_inverval_multipliers | u(8) |
|   for (i=0; i<num_interval_multipliers; i++); | |
|     interval_multipliers[i] | u(32) |
|   } | |
|   num_norm_methods | u(8) |
|   for (i=0; i<num_weights;i++){ | |
|     norm_methods_id[i] | u(8) |
|     norm_methods_name[i] | st(v) |
|     norm_methods_mult_flag[i] | u(1) |
|     reserved | u(7) |
|   } | |
|   num_norm_matrices | u(8) |
|   for (i=0; i<num_normval;i ++){ | |
|     norm_matrices_id[i] | u(8) |
|     norm_matrices_name[i] | st(v) |
|   } | |
| } | |

In the above CMC header syntax, the following are examples of the values that can be used:
  dataset_id specifies the identifier of the dataset.
  num_samples is the number of samples in the dataset.
  samples_id[i] is the identifier of the sample with index i.
  samples_name[i] is the name of the sample with index i.
  num_chrs is the number of chromosomes in the dataset.
  chrs_id[i] is the identifier of the chromosome with index i.
  chrs_name[i] is the name of the chromosome with index i.

chrs_length[i] is the length of the chromosome with index i.

interval is the bin size of the contact matrix structure.

tile_size is the maximum number of entries in row and column direction per contact matrix tile specified herein.

num_inverval_multipliers is the number of entries of array interval_multipliers[ ]. If num_interval_multipliers is greater than 1, the structure supports multiple intervals.

interval_multipliers[i] is the interval multiplier supported by this structure at index i num_norm_methods is the number the normalization methods which weights are stored.

norm_methods_id[i] is the identifier of the normalization method with index i which weights are stored in the structure specified herein.

norm_methods_name[i] is the name of the normalization method with index i which weights are stored.

norm_methods_mult_flag[i] if set to 1, it signals that during the on-the-fly normalization each entry of the contact matrix tile must be multiplied by the product of two weights. Otherwise, each entry of the contact matrix tile must be divided by the product of two weights.

num_norm_matrices is the number of normalized matrices stored.

norm_matrices_id[i] is the identifier of the normalized matrix with index i.

norm_matrices_name[i] is the name of the normalized matrix with index i.

num_bin_entries is the number of bins of the chromosome with the identifier chr_id and depends on interval multiplier and interval. It is computed as follows:

Ceil(chr_length[chr_id]/ (interval_multiplier*interval)).

num_tiles is the number of tiles of the chromosome with the identifier chr_id given interval, interval multiplier and tile_size. It is computed as follows:

Ceil(num_bin_entries/tile_size).

target_tile_size is the decoded or target_tile_size given multiplier mult. It is computed as follows: target_tile_size=Floor(tile_size/mult).

target_interval is the interval of decoded tile. It is computed as follows: target_interval=interval*mult.

target_chr_len is the chromosome length chrs_length[i] with index i given chromosome id chr_id equals to chrs_id[i].

Next is disclosed the CMC bin payload syntax corresponding to feature 1504 in FIG. 15.

| Syntax | Type |
| --- | --- |
| cmc_bin_payload( ){ | |
|   chr_id | u(8) |
|   sample_id | u(8) |
|   interval_multiplier | u(32) |
|   for (i =0; i<num_norm_methods; i++){ | |
|     for (j =0; j<num_bin_entries; j++){ | |
|       weight_values[i][j] | f(64) |
|     } | |
|   } | |
| } | |

The following are example values for the bin payload syntax:

chr_id is the identifier of the chromosome.

sample_id is the identifier of the sample.

interval_multiplier specify the multiplier of the interval to compute the num_bin_entries. The valid values for interval_multiplier is one of the entries of the array interval_multipliers[ ] specified above.

num_norm_methods is the number the normalization methods which weights are stored, specified herein.

num_bin_entries is the number of bins of the chromosome with the identifier chr_id and depends on interval_multiplier and interval. It is specified above.

weight_values[i][j] is the $j^{th}$ weight value of the $i^{th}$ normalization method.

Next is disclosed an example of the syntax that can be used for the CMC parameter set 1506 shown in FIG. 15.

| Syntax | Type |
| --- | --- |
| cmc_param_set( ){ | |
|   param_set_id | u(16) |
|   chr1_id | u(8) |
|   chr2_id | u(8) |
|   for (i=0; i<ntiles_in_row; i++){ | |
|     for (j=0; j<ntiles_in_col; j++){ | |
|       if (is_symmetrical && i>j){ | |
|         continue | |
|       } | |
|       diag_transform_flags[i][j] | u(1) |
|       if (diag_transform_flags[i][j]){ | |
|         diag_transform_modes[i][j] | u(2) |
|       } | |
|       binarization_flags[i][j] | u(1) |
|     } | |
|   } | |
|   row_mask_exists_flag | u(1) |
|   col_mask_exists_flag | u(1) |
|   while(!byte_aligned( )){ | |
|     nesting_zero_bit | u(1) |
|   } | |
| } | |

An example of the various values for these parameters can include:

param_set_id is the identifier of the contact matrix parameter set.chr1_id is the identifier of the first chromosome of the chromosome pair.

chr2_id is the identifier of the second chromosome of the chromosome pair.

ntiles_in_row equals num_tiles for chromosome with identifier chr1_id. num_tiles is specified above.

ntiles_in_col equals num_tiles for chromosome with identifier chr2_id. num_tiles is specified above.

is_symmetrical is set to 1 if chr1_id equals chr2_id, otherwise 0.

diag_transform_flags[i][j] if set to 1, it signals that diagonal transformation is applied to the contact matrix tile structure specified below with index i for the first dimension and index j for the second dimension.

diag_transform_modes[i][j] specifies the diagonal transformation mode for the contact matrix tile structure specified below with index i for the first dimension and index j for the second dimension.

binarization_flags[i][j] if set to 1, it signals that binarization is done to the contact matrix tile structure specified below with index i for the first dimension and index j for the second dimension.

row_mask_exists_flag if set to 1, it signals that row_mask_payload exists in the contact matrix payload structure specified below.

col_mask_exists_flag if set to 1, it signals that col_mask_payload exists in the contact matrix payload structure specified below.

Next is disclosed an example syntax for the CMC Matrix Payload 1508 shown in FIG. 15.

| Syntax | Type |
|---|---|
| cmc_mat_payload( ){ | |
|   param_set_id | u(16) |
|   sample_id | u(8) |
|   for(i=0; i<ntiles_in_row; i++){ | |
|     for(j=0; j<ntiles_in_col; j++){ | |
|       if (is_symmetrical && i>j) { | |
|         continue | |
|       } | |
|       tile_payload_sizes[i][j] | u(32) |
|       tile_payloads[i][j] | cmc_tile_payload( ) |
|     } | |
|   } | |
|   for (k=0; k< num_norm_matrices; k++){ | |
|     for(i=0; i<ntiles_in_row; i++){ | |
|       for(j=0; j<ntiles_in_col; j++){ | |
|         if (is_symmetrical && i>j) { | |
|           continue | |
|         } | |
|         norm_matrix_payload_sizes[k][i][j] | u(32) |
|         norm_matrix_payloads[k][i][j] | codec_payload( ) |
|       } | |
|     } | |
|   } | |
|   if (row_mask_exists_flag){ | |
|     row_mask_payload_size | u(32) |
|     row_mask_payload | cmc_mask_payload( ) |
|   } | |
|   if (!is_symmetrical && col_mask_exists_flag){ | |
|     col_mask_payload_size | u(32) |
|     col_mask_payload | cmc_mask_payload( ) |
|   } | |
| } | |

An example of the various values for these parameters can include:

param_set_id is the identifier of the cmc parameter set specified above used to decode the content of cmc matrix payload.

sample_id is the identifier of the sample. Samples are specified in cmc header structure above.

ntiles_in_row equals num_tiles for chromosome with identifier chr1_id. num_tiles as specified above.

ntiles_in_col equals num_tiles for chromosome with identifier chr2_id. num_tiles as specified above.

is_symmetrical is set to 1 if chr1_id equals to chr2_id, otherwise 0.

tile_payload_sizes[i][j] is the size in bytes of the contact matrix payload structure as specified below, with index i and j.

tile_payloads[i][j] is the contact matrix tile payload structure as specified below with index i and j.

num_norm_matrices is the number of normalized matrices stored in cmc matrix payload structure specified above.

norm_matrix_payload_sizes[k][i][j] is the size in bytes of the compressed $k^{th}$ normalized contact matrix with index i and j.

norm_matrix_payloads[k][i][j] is the payload of the compressed $k^{th}$ normalized contact matrix with index i and j.

row_mask_payload_size is the size in bytes of the mask payload structure as specified below.

row_mask_payload is the mask payload structure as specified below.

col_mask_payload_size is the size in bytes of the mask payload structure as specified below.

col_mask_payload is the mask payload structure as specified below. If the is_symmetrical of the corresponding parameter set is set to 1, the content of col_mask_payload is identical to the row_mask_payload and therefore not stored.

Next is disclosed an example CMC tile payload syntax.

| Syntax | Type |
|---|---|
| cmc_tile_payload( ){ | |
|   tile_nrows | u(32) |
|   tile_ncols | u(32) |
|   payload | codec_payload( ) |
| } | |

An example of the various values for these parameters can include:

tile_nrows is the number of rows of the contact matrix tile structure.

tile_ncols is the number of columns of the contact matrix tile structure.

payload is the payload of the compressed cmc tile. The content depends on the codec of choice.

Next is disclosed an example CMC mask payload syntax.

| Syntax | Type |
|---|---|
| cmc_mask_payload( ){ | |
|   transform_id | u(2) |
|   if (transform_id == 0){ | |
|     for (i=0; i<num_bin_entries; i++){ | |

| Syntax | Type |
|---|---|
|       mask_array[i] | u(1) |
|     } | |
|   } | |
|   else { | |
|     first_val | u(1) |
|     for (k=0; k<num_rl_entries; k++){ | |
|       rl_content[k] | u(nbits_per_val) |
|     } | |
|   } | |
|   while(!byte_aligned( )){ | |
|     nesting_zero_bit | |
|   } | |
| } | |

An example of the various values for these parameters can include:

transform_id if set to >0, it signals that mask_payload structure is transformed using run-length encoding. The number of bits required to store each value of mask_payload structure and whether the payload is run-length encoding transformed is specified below.

num_bin_entries is the number of bins of the chromosome with the identifier chr_id and depends on interval_multiplier and interval, specified above.

mask_array[i] is the mask array value at index i.

The following table illustrates a transform_id and associated transformation flags and parameters.

| transform_id | Transformed using run-length | nbits_per_val |
|---|---|---|
| 0 | false | 1 |
| 1 | true | 8 |
| 2 | true | 16 |
| 3 | true | 32 |

The first val can be the first value of the cmc mask_payload structure if transform_id!=0. The first value is used to inverse transform the run-length encoded mask array. The value rl_content[k] can be the value of run-length at index k.

Next is discussed an example decoding process. This section describes the decoding process of contact matrix 1500. The inputs of this process are:
- cmc header header specified above.
- cmc parameter set param_set specified above.
- cmc matrix payload mat_payload specified above.
- interval_multiplier mult.
- cmc bin payload bin_payload1 specified above with chr_id equals to param_set.chr1_id, sample_id equals to mat_payload.sample_id and interval_multiplier equals to mult.
- cmc bin payload bin_payload2 specified above with chr_id equals to param_set.chr2_id, sample_id equals to mat_payload.sample_id and interval_multiplier equals to mult.

The above input can be viewed as example of a decoding process in which the steps of the process can include receiving the contact matrix data structure and performing a decoding of the contact matrix data structure based on a desired pair of chromosomes, a desired interval represented as an interval multiplier and computed by: interval_high (i.e., the desired interval)=interval_multiplier (i.e., an input for the decoding process)*interval_low (i.e., data from the header). An output of the decoding process can be a contact matrix with one or more values or characteristics mentioned next.

The output of this process is a contact matrix in sparse representation:
- The identifier of sequence 1 chr1_id equals to param_set.chr2_id.
- The array of start position values of sequence 1 start1 [ ].
- The array of end position values of sequence 1 end1 [ ].
- The identifier of sequence 2 chr2_id equals to param_set.chr2_id.
- The array of start position values of sequence 2 start2[ ].
- The array of end position values of sequence 2 end2[ ].
- The array of count values count[ ].
- 2-dimensional array norm_mats_otf[ ][ ] if header.num_norm_methods is greater than 1.
- 2-dimensional array norm_mats[ ][ ] if header.num_norm_matrices is greater than 1.

The following illustrates an example syntax for decoding the contact matrix 1500.

| Syntax | Remarks |
|---|---|
| decode_contact_matrix(header, param_set, mat_payload, mult){ | |
|   row_mask, col_mask = decode_cmc_masks(header, parameter_set, mat_payload) | |
|   start1[ ] = [ ] | Initialize empty array |
|   end1[ ] = [ ] | Initialize empty array |
|   start2[ ] = [ ] | Initialize empty array |
|   end2[ ] = [ ] | Initialize empty array |
|   count[ ] = [ ] | Initialize empty array |
|   for (k=0; k<header.num_norm_methods; k++) | Initialize empty array |
|     norm_mats_otf[k][ ] = [ ] | |
|   } | |
|   for (k=0; k<header.num_norm_matrices; k++) | |

-continued

| Syntax | Remarks |
|---|---|
|     norm_mats[k][ ] = [ ]<br>}<br>for (i=0; i<param_set.ntiles_in_row; i++){<br>  for (j=0; j<param_set.ntiles_in_col; j++){<br>    if (param_set.is_symmetrical && i>j){<br>      continue<br>    }<br>    if (mat_payload.tile_payload_sizes[i][j]== 0){<br>      continue | Initialize empty array<br><br><br><br><br><br><br><br>Skip the process as the tile contains no information |
|     }<br>    tile = decode_cmc_tile(<br>        mat_payload.tile_payloads[i][j],<br>        param_set.binarization_flags[i][j]<br>      )<br>    if (param_set.binarizaton_flags[i][j]){<br>      tile = debinarize_mat(tile) | Specified in the Decode CMC Tile process syntax<br><br><br><br>Specified in the Debinarize Tile process syntax |
|     }<br>    if (param_set.diagonal_transform_flags [i][j]){<br>      tile = inv_diag_transform(<br>        tile,<br>        param_set.diagonal_tranform_modes[i][j]<br>      )<br>    } | Specified in the inverse diagonal transform process syntax |
|     [start1_idx, end1_idx] = comp_start_end_idx(<br>        header,<br>        param_set.chr1_id,<br>        1,<br>        i) | Specified in the compute start end index process syntax |
|     [start2_idx, end2_idx] = comp_start_end_idx(<br>        header,<br>        param_set.chr2_id,<br>        1,<br>        j) | Specified in the compute start end index process syntax |
|     tile_row_mask = slice(row_mask, start1_idx, end1_idx) | Specified in the slice mask syntax |
|     tile_col_mask = slice(col_mask, start2_idx, end2_idx) | Specified in the slice mask syntax |
|     if (mult != 1){<br>      tile = conv_noop(tile, mult, tile_row_mask,<br>          tile_col_mask)<br>      [tmp_nrows, tmp_ncols] = Shape(tile)<br>      tile_row_mask = create_ones_mask(tmp_nrows) | Specified in the Convolution no-OP.<br>Get shape size<br>Specified in the create ones mask syntax |
|       tile_col_mask = create_ones_mask(tmp_ncols) | Specified in create ones mask syntax |
|       [start1_idx, end1_idx] = comp_start_end_idx(<br>        header,<br>        param_set.chr1_id,<br>        mult,<br>        i) | Specified in the compute start end index process syntax |
|       [start2_idx, end2_idx] = comp_start_end_idx(<br>        header,<br>        param_set.chr2_id,<br>        mult,<br>        i) | Specified in the compute start end index process syntax |
|     }<br>    start1_arr = comp_start(header, mult, start1_idx,<br>        end1_idx, tile_row_mask) | Specified in the compute start array syntax |
|     end1_arr = comp_end(start1_arr, header, mult,<br>        paramset.chr1_id) | Specified in the compute end array syntax |
|     start2_arr = comp_start(header, mult, start2_idx,<br>        end2_idx, tile_col_mask) | Specified in the compute start array syntax |
|     end2_arr = comp_end(start2_arr, header, mult,<br>        param_set.chr2_id) | Specified in the compute end array syntax |
|     [start1_desc, end1_desc,<br>     start2_desc, end2_desc,<br>     count_desc] = tile_to_desc (tile,<br>        start1_arr, end1_arr, | Specified in the tile to descriptor syntax |

-continued

| Syntax | Remarks |
|---|---|
|                 start2_arr, end2_arr)<br>    start1 = Cat(start1, start1_desc)<br>    end1 = Cat(end1, end1_desc)<br>    start2 = Cat(start2, start2_desc)<br>    end2 = Cat(end2, end2_desc)<br>    count = Cat(count, count_desc)<br>    for (k=0; k<header.num_norm_methods; k++){<br>      mult_flag = header_norm_methods_mult_flag[k]<br>      weight_values1 = bin_payload1.weight_values[k]<br>      tile_weight_vals1 = slice(weight_values1,<br>                start1_idx, end1_idx)<br>      weight_values2 = bin_payload2.weight_values[k]<br>      tile_weight_vals2 = slice(weight_values2,<br>                start2_idx, end2_idx) | Specified in the slice mask syntaxError! Reference source not found. |
|       ith_norm_tile = comp_otf_norm_mat(tile,<br>                tile_row_mask,<br>                tile_col_mask,<br>                tile_weight_vals1,<br>                tile_weight_vals2,<br>                mult_flag)<br>      norm_mats_otf[k] = Cat(norm_mats_otf[k],<br>                ith_norm_tile)<br>    }<br>    for (k=0; k<header.num_norm_matrices; k++){<br>      ith_data = decode( | Compute on-the-fly normalization. Specified in the compute on-the-fly normalized tile syntax |
|         mat_payload.norm_matrix_payloads[k][i][j])<br>      norm_mats[k] = Cat(norm_mats[k], ith_data)<br>    }<br>  }<br>  }<br>} | Use decoder specific decoding process and parameter set |

Next is discussed a process of decoding the CMC mask and the associated syntax. The inputs of this process are:
    cmc header header specified above.
    cmc parameter set param_set specified above.
    cmc matrix payload mat_payload specified above.

The output of this process are arrays row_mask[ ] and col_mask[ ]. The following is the decode CMC mask syntax.

| Syntax | Remarks |
|---|---|
| decode_cmc_masks (header, param_set, mat_payload){<br>  row_nentries = header.num_bin_entries | Given param_set.chr1_id, multiplier equals 1 |
|   if (param_set.row_mask_exists_flag){<br>    row_mask = decode_mask(<br>      mat_payload.row_mask_payload,<br>      row_nentries<br>    )<br>  }<br>  else {<br>    for(i=0; i<row_nentries; i++){<br>      row_mask[i] = 1<br>    }<br>  }<br>  col_nentries = header.num_bin_entries | Specified in Error! Reference source not found. |
|   if (param_set.is_symmetrical){<br>    for(i=0; i<row_nentries; i++){ | Given param_set.chr2_id, multiplier equals to 1<br><br>Because the masks are identical, using either row_nentries or col_nentries is allowed |
|       col_mask[i] = row_mask[i]<br>    }<br>  } else if (param_set.col_mask_exists_flag){ | |

| Syntax | Remarks |
|---|---|
| ```
    col_mask = decode_mask(
        mat_payload.col_mask_payload,
        col_nentries
    )
  } else {
    for(i=0; i<col_nentries; i++){
      col_mask[i] = 1
    }
  }
}
``` | Specified in Error! Reference source not found. |

In another aspect, a decoding process for the CMC mask can receive as inputs:
  cmc mask payload mask_payload specified herein.
  number of entries num_entries of the array mask[ ].
The output of this process is an array mask[ ].
Next is disclosed this aspect of the process of decoding the CMC mask.

| Syntax | Remarks |
|---|---|
| ```
decode_cmc_mask(mask_payload, num_entries){
  if (mask_payload.mask_transform_id == 0){
    for (i=0; i<num_entries; i++){
      mask[i] = mask_array[i]
    }
  }
  else {
    mask_val = mask_payload.first_val
    i = 0
    for (k=0; k<mask_payload.num_rl_entries; k++){
      for (j=0; j<rl_content[k]; j++){
        mask[i] = mask_val
        i++
      }
      mask_val = !mask_val
    }
    while (i<num_entries){
      mask[i] = mask_val
      i++
    }
  }
}
``` | Copy the array<br><br><br><br>u(1)<br><br><br>u(1)<br><br><br><br>Invert value |

Next is discussed the process of decoding the CMC tile 1510. The input of this process are:
  cmc tile payload structure tile_payload specified above.
  binarization flag bin_flag.
The output of this process is a 2-dimensional array tile [ ][ ]. The following is an example of the syntax for decoding the CMC tile 1508.

| Syntax | Remarks |
|---|---|
| ```
decode_cmc_tile(tile_payload, bin_flag){
  decoded_symbols[ ] = decode(payload)
  k = 0
``` | Use codec specific decode function |

| Syntax | Remarks |
|---|---|
| ```
  for (i=0; i< tile_payload.tile_nrows; i++) {
    for (j=0; j< tile.payload.tile_ncols; j++) {
      tile[i][j] = decoded_symbols[k]
      k = k + 1
    }
  }
}
``` | u(var) |

In this syntax, the var is the bitlength of each entry in the decoded symbol. var depends on binarization_flag. If binarization_flag is 1, then var is equal to 1. Otherwise, it is 32.

Next is discussed the process of performing a debinarizing of the tile 1508. The input of this process is a 2-dimensional array tile[ ][ ]. The output of this process is a 2-dimensional array trans_tile[ ][ ]. The example syntax is as follows:

| Syntax | Remarks |
|---|---|
| ```
debinarize_tile (tile){
  [tile_nrows, tile_ncols] = Shape(tile)

i_out = 0
  bit_pos = 0
  for(i=0; i< tile_nrows; i++){
    for (j=1; j< tile_ncols; j++) {
      trans_tile[i_out][j-1] = tile[i][j] << bit_pos
    }
    if (tile[i][0] == 1) {
      i_out += 1
      bit_pos = 0
    }
    else {
      bit_pos += 1
    }
  }
}
``` | Get the dimensions of tile |

Next is discussed a process of performing an inverse diagonal transform. The input of this process are: a 2-dimensional array tile[ ][ ] and the diagonal transform mode 1400. The output of this process is a 2-dimensional array trans_tile[ ][ ]. Example syntax for this transform process follows:

| Syntax | Remarks |
|---|---|
| ```
inv_diag_transform (tile, mode){
  if (mode == 0) {
    [unused_var, ncols] = Shape(tile)

num_diags = ncols
``` | Get the dimensions of tile |

-continued

| Syntax | Remarks |
|---|---|
| ```
      k = 0
      l = 0
      for (k_diag=0; k_diag<num_diags; k_diag++){
        if (k >= ncols){
          break
        }
        if (k_diag > 0) {
          j_offset = k_diag
        }
        else {
          j_offset = 0
        }
        end_diag = ncols − j_offset
        for (i=0; i< end_diag; i++){
          j = I + j_offset
          trans_tile[i][j] = tile[k][l]
          l += 1
          if (l == ncols){
            l = 0
            k += 1
            if (k >= ncols){
              break
            }
          }
        }
      }
    else {
      [nrows, ncols] = Shape(tile)
      num_diags = Max(nrows, ncols)
      if (mode==1) {
        diag_idx = [0]
        i = 1
        for (k=1; k<num_diags; k++){
          if (k<ncols) {
            diag_idx[i] = k
            i++
          }
          if (k<nrows) {
            diag_idx[i] = −k
            i++
          }
        }
      }
      else if (mode==2) {
        i = 0
        for (k=−(num_diags−1); k<num_diags; k++) {
          diag_idx[i] = k
          i++
        }
      }
      else if (mode==3) {
        i = 0
        for (k=num_diags−1; k>−num_diags; k−−) {
          diag_idx[i] = k
          i++
        }
      }
      k = 0
      l = 0
      for (o = 0; o < Size(diag_idx); o++) {
        diag_id = diag_idx[o]
        if (diag_id > 0) {
          i_offset = 0
          j_offset = diag_id
        }
        else if (diag_id < 0) {
          i_offset = −diag_id
          j_offset = 0
        }
        else if (diag_id == 0) {
          i_offset = 0
          j_offset = 0
        }
        end_diag = Min(nrows−i_offset,
                ncols−j_offset)
        for (k_diag=0; k_diag<end_diag; k++) {
          i = k_diag + i_offset
``` | Get the dimensions of tile |

| Syntax | Remarks |
|---|---|
| ```
        j = k_diag + j_offset
        trans_tile[i][j] = tile[k][l]
        l ++
        if (l == ncols){
          l = 0
          k += 1
        }
      }
    }
  }
}
``` | |

Next is disclosed a process to compute a start-end index. The input of this process are: cmc header header specified above; chromosome id chr_id; multiplier mult; and a tile index tile_idx. The output of this process are integer start_idx and end_idx. The following is an example syntax:

| Syntax | Remarks |
|---|---|
| ```
comp_start_end_idx (header, chr_id, mult, tile_idx){
  nentries = header.num_bin_entries
``` | Given chromosome id chr_id and multiplier mult |
| ```
  target_tile_size = header.target_tile_size
``` | Given multiplier mult |
| ```
  start_idx = tile_idx * target_tile_size
  end_idx = Min(nentries, start_idx + target_tile_size)
}
``` | |

Next is discussed a process associated with slicing a mask. The input of this process are: array mask[ ]; start index start_idx; end index and end_idx. The output of this process is an array sliced_mask[ ]. The example syntax follows:

| Syntax | Remarks |
|---|---|
| ```
slice(mask, start_idx, end_idx){
  nentries = Size(mask)
  j = 0
  for (i = 0; i<nentreis; i++) {
    if (start_idx <= i && i<end_idx){
      sliced_mask[j] = mask[i]
      j++
    }
  }
}
``` | |

Next is discussed a process of computing a start array. The input of this process are: cmc header header specified above; multiplier mult; start index start_idx; end index end_idx and array tile mask[ ]. The output of this process is an array start_arr[ ]. The example syntax follows:

| Syntax | Remarks |
|---|---|
| ```
comp_start (header, mult, start_idx, end_idx, tile_mask){
  target_interval = header.target_interval
``` | Given multiplier mult |
| ```
  i = 0
  j = 0
  for (idx=start_idx; idx<end_idx; idx++){
    if (tile_mask[i] == 1){
``` | |

| Syntax | Remarks |
|---|---|
| ```
        start_arr[j] = idx*target_interval
        j++
      }
      i++
    }
}
``` | |

Next is discussed a process of computing an end array. The input of this process are: array start_arr[ ]; cmc header header specified above; multiplier mult and chromosome id chr_id. The output of this process is an array end_arr[ ]. The example syntax follows:

| Syntax | Remarks |
|---|---|
| comp_end (start_array, header, mult, chr_id){ | |
|   nentries = Size(start_array) | |
|   target_interval = header.target_interval | Given multiplier mult |
|   target_chr_len = header.target_chr_len | Given chromosome id chr_id |
|   for (i = 0; i<nentries; i++){ | |
|     end_arr[i] = start_arr[i] | |
|   } | |
|   end_arr[nentries−1] = Min(end_arr[nentries−1], target_chr_len) | |
| } | |

Next is discussed a convolution process without operation method 0109. The input of this process are: 2-dimensional array tile[ ][ ]; window size ws; array tile_row_mask[ ] and array tile_col_mask[ ]. The output of this process is an array end_arr[ ]. The syntax is as follows:

| Syntax | Remarks |
|---|---|
| ```
conv_noop (tile, ws, tile_row_mask, tile_col_mask){
  [nrows, ncols] = Shape(tile)
  i_tile = 0
  for (i_ttile=0;i_ttile<nrows;i_ttile++){
    any_in_row = 0
    i_ottile = Floor(i_ttile/ws)
    j_tile = 0
    for (j_ttile=0;j_ttile<ncols;j_ttile++){
      if (tile_col_mask[j_ttile]){
        if (tile_row_mask[i_ttile]){
          any_in_row = 1
          j_ottile = Floor(j_ttile/ws)
          out_ttile[i_ottile, j_ottile] += tile[i_tile,
              j_tile]
        j_tile += 1
      if (any_in_row]
        i_tile += 1
      }
    }
  }
}
``` | |

Next is discussed a process of creating a ones mask. The input of this process is: number of entries nentries. The output of this process is an array mask[ ]. The example syntax follows:

| Syntax | Remarks |
|---|---|
| create_ones_mask (nentries)} | |
|   if (i=0;i<nentries;i++){ | |
|     mask[i] = 1 | |
|   } | |
| } | |

Next is disclosed a tile to descriptor process. The input of this process are: 2d-array tile[ ][ ]; array start1_arr[ ]; array end1_arr[ ]; array start2_arr[ ]; and array end2_arr[ ]. The output of this process are arrays start1_desc[ ], end1_desc[ ], start2_desc[ ], end2_desc[ ] and count_desc[ ]. The example syntax follows:

| Syntax | Remarks |
|---|---|
| tile_to_desc (tile, start1_arr, end1_arr, start2_arr, end2_arr){ | |
|   [nrows, ncols] = Shape(tile) | |
|   nentries = 0 | |
|   for (i=0; i<nrows; i++){ | |
|     for (j=0; j<ncols; j++){ | |
|       if (tile[i][j] !=0){ | |
|         start1_desc[nentries] = start1_arr[i] | |
|         end1_desc[nentries] = end1_arr[i] | |
|         start2_desc[nentries] = start2_arr[j] | |
|         end2_desc[nentries] = end2_arr[j] | |
|         count_desc[nentries] = tile[i][j] | |
|         nentries++ | |
|       } | |
|     } | |
|   } | |
| } | |

Next is disclosed an approach to computing an on-the-fly normalized tile. The input of this process are: 2-dimensional array tile[ ][ ]; array row_mask[ ]; array col_mask[ ]; array weight_values1[ ]; array weight_values2[ ]; and flag mult_flag. The output of this process is an array norm_counts[ ]. The syntax follows:

| Syntax | Remarks |
|---|---|
| ```
comp_otf_norm_mat (tile, row_mask, col_mask, weight_values1,
            weight_values2, mult_flag){
  nrows = Shape(row_mask)
  ncols = Shape(col_mask)
  nentries = 0
  t_i = 0
  for (i=0; i<nrows; i++){
    if (row_mask[i] != 1){
      continue
    }
    t_j = 0
    for (j=0; j<ncols; j++){
      if (col_mask[j] != 1){
        continue
      }
      if (tile[t_i][t_j] != 0){
        weight = weight_values1[i] * weight_values2[j]
        if (mult_flag == 1){
          norm_counts[nentries] = tile[t_i][t_j] * weight
        } else {
          norm_counts[nentries] = tile[t_i][t_j] / weight
        }
        nentries++
      }
      t_j=++
    }
    t_i++
  }
}
``` | |

Any of the syntax described above can be included in any encoding or decoding method or system embodiments. The syntax or a portion of any of the syntax can be claimed independent of other sections of any syntax.

FIG. 18 illustrates a method 1800 for decoding a contact matrix. The method 1800 can include receiving a contact matrix data structure, wherein the contact matrix data structure can include one or more of: a header containing an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payload (1802) and, based on the contact matrix data structure, a desired pair of chromosomes and a desired interval multiplier corresponding to a desired interval of an output contact matrix, generating the output contact matrix (1804). The identifiers can be an identifier of a first sequence (or chromosome) of a chromosome pair. The value is stored in the parameter set.

The output contact matrix can include:
an identifier of sequence 1 chr1_id;
an array of start position values of sequence 1 start1 [ ];
an array of end position values of sequence 1 end1 [ ];
an identifier of sequence 2 chr2_id;
an array of start position values of sequence 2 start2[ ];
an array of end position values of sequence 2 end2[ ];
an array of count values count[ ];
a 2-dimensional array norm_mats_otf[ ][ ] if header. num_norm_methods is greater than 1; and
a 2-dimensional array norm_mats[ ][ ] if header. num_norm_matrices is greater than 1. an identifier of sequence 2 chr2_id.

The identifier above can be an identifier of the second sequence (or chromosome) of the chromosome pair. The value norm_mats_otf[ ][ ] is a list of normalized contact matrix that is computed using the on-the-fly normalization method. This can be a part of the output if it is signaled that any on-the-fly normalization was done (i.e., the value of num_norm_methods is greater than one). The num_norm_methods can be a part of a header. The value norm_mat[ ] [ ] can be a list of normalized contact matrix that is decoded from precomputed normalized contact matrix. This is a part of the output if it is signaled that any precomputed normalization was done (i.e., the value num_norm_matrices is greater than one). The num_norm_matrices can be a part of a header.

The chr1_id and the chr2_id each represent a respective identifier of a respective chromosome. The header. num_norm_methods can be a number of on-the-fly normalization methods for which weights are stored in the zero or more bin payload described in the header. The header. num_norm_matrices can be a number of precomputed normalized contact matrix described in the header. The interval_multiplier specifies a multiplier of an interval to compute a number of bin entries.

The parameter set can include an identifier parameter set used to decode the at least one matrix payload. The parameter set can be the parameter set with a specific identifier.

The matrix payload can include one or more tile payloads having content depending on a chosen compression method, zero or more precomputed normalized tile payloads, zero or one row mask payload and zero or one column mask payload. The output contact matrix can include at least one two-dimensional array tile representing a tile payload.

The interval_multiplier can be used to compute larger intervals from a smaller interval contact matrix by: interval_high=interval_multiplier*interval_low. The interval_high can be the desired interval. The interval_multplier can be the input for the decoding process and the interval_low can be data from the header.

The count[ ] can be computed by: decoding and transforming tile payload associated to the matrix payload and parameter set; summing the values within non-overlapping window with window size equals to interval_multiplier if the interval_multiplier is greater than one to yield results; and concatenating all of the results from all tiles.

The norm_mats_otf[ ][ ] can be computed by: decoding and transforming tile payload associated to the matrix payload and parameter set; summing the values within non-overlapping window with window size equals to interval_multiplier if the interval_multiplier is greater than one; and multiplying with the weights stored in the bin payload by: $T\_i\_j=w\_i*w\_j*A\_i\_j$ if the associated norm_methods_mult_flag is 1, otherwise $T\_i\_j=A\_i\_j/(w\_i*w\_j)$ to yield results; and concatenating all of the results from all tiles.

The interval_multiplier can be a positive integer and a factor of a tile size associated with the matrix tile payload. The interval_low can be the interval described in the header structure described herein.

The interval_high can be the desired interval described herein. The $A\_i\_j$ above can be the value of a 2-dimensional array tile at row i and column j. The $w\_i$ can be the i-th above can be the weight of the associated on-the-fly normalization method. The $w\_j$ can be the j-th weight can be related to the associated on-the-fly normalization method. The $T\_i\_j$ can be the value of a 2-dimensional array normalized tile at row i and column j.

One aspect of this disclosure can include a system including a processor and a computer-readable storage device storing a contact matrix data structure. The contact matrix data structure can include a header containing one or more of an interval of a contact matrix, a list of interval multipliers, a tile size, a list of chromosomes with a corresponding identifier and length, a list of sample identifiers, zero or more names of methods of normalization performed on the contact matrix tiles; zero or more bin payload having an interval multiplier; at least one parameter set; and at least one matrix payloads. In one aspect, the number of parameter sets can equal the number of matrix payloads. The contact matrix data structure is shown by way of example in FIG. 15.

A content of the contact matrix can include a number of contacts or interactions within a certain genomic region. See FIG. 1B for the example of the contact or interactions within the certain genomic region. An interval of the contact matrix can refer to a bin size of the contact matrix.

The name of the method of normalization performed on the contact matrix tile can refer to one of an on-the fly normalization method or a precomputed normalization method.

The interval multiplier can be associated with weights corresponding to a same or higher interval. In one case, the multiplier can equal 1. The bin payload further can include one or more weights for each of a plurality of on-the-fly normalization methods. The interval multiplier can include a positive integer and is a factor of the tile size. In one aspect, the interval multiplier is used in a decoding process by applying the interval multiplier to obtain a summation of all entries within one square window to compute an entry of a contact matrix tile with a higher interval by adding all entries in the window.

The parameter set can include a parameter set identifier, a first chromosome of a chromosome pair and a second chromosome of the chromosome pair. The number of rows and columns are typically computed. The matrix payload can include one or more tile payloads, zero or more precomputed normalized tile payloads, zero or one row mask payload and zero or one column mask payload.

One embodiment disclosed herein can include a system including a processor; and a computer-readable storage device storing a contact matrix and related information and a program for generating a contact matrix structure according to any of the concepts disclosed herein. The system can be an encoder that performs encoding operations to generate the contact matrix structure.

As noted above, embodiments can include systems and methods for coding a contact matrix. An example coding method can include coding a contact matrix data structure from a contact matrix, the contact matrix data structure including: a header containing an interval of a contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payloads. The method can include receiving the contact matrix and, based on the contact matrix, generating the contact matrix data structure.

An example encoder can include a system including a processor and a computer-readable storage device storing a contact matrix, related information and program instructions wherein the program instructions, when executed by the processor, cause the processor to perform operations. The operations can include receiving the contact matrix from the computer-readable storage device and, based on the contact matrix, generating a contact matrix structure, wherein the contact matrix structure comprises: a header containing an interval of the contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payloads.

Related information that can be used in encoding (or decoding) the contact matrix structure can include one or more of a list of chromosomes, a normalization method, a tile size, weights and interval values. Weights for the corresponding interval value and normalization method may be computed during the encoding process. The encoder may read information that defines the interval numbers, corresponding weights and normalization methods from file.

The computing device (or apparatus) for encoding or decoding can include any suitable device, such as a mobile device (e.g., a mobile phone), a desktop computing device, a tablet computing device, a server computer, a laptop computer, and/or any other computing device with the resource capabilities to perform the processes described herein, including the process 1800 and/or any other process described herein. In some cases, the computing device or apparatus may include various components, such as one or more input devices, one or more output devices, one or more processors, one or more microprocessors, one or more microcomputers, one or more sensors, and/or other component(s) that are configured to carry out the steps of processes described herein. In some examples, the computing device may include a display, a network interface configured to communicate and/or receive the data, any combination thereof, and/or other component(s). The network interface may be configured to communicate and/or receive Internet Protocol (IP) based data or other type of data.

The components of the computing device can be implemented in circuitry. For example, the components can include and/or can be implemented using electronic circuits or other electronic hardware, which can include one or more programmable electronic circuits (e.g., microprocessors, graphics processing units (GPUs), digital signal processors (DSPs), central processing units (CPUs), and/or other suitable electronic circuits), and/or can include and/or be implemented using computer software, firmware, or any combination thereof, to perform the various operations described herein.

The process 1800 is illustrated as a logical flow diagram, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the process 1800 and/or any other process described herein may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable or machine-readable storage medium, for example, in the form of a computer program comprising a plurality of instructions executable by one or more processors. The computer-readable or machine-readable storage medium may be non-transitory.

Figure 19:
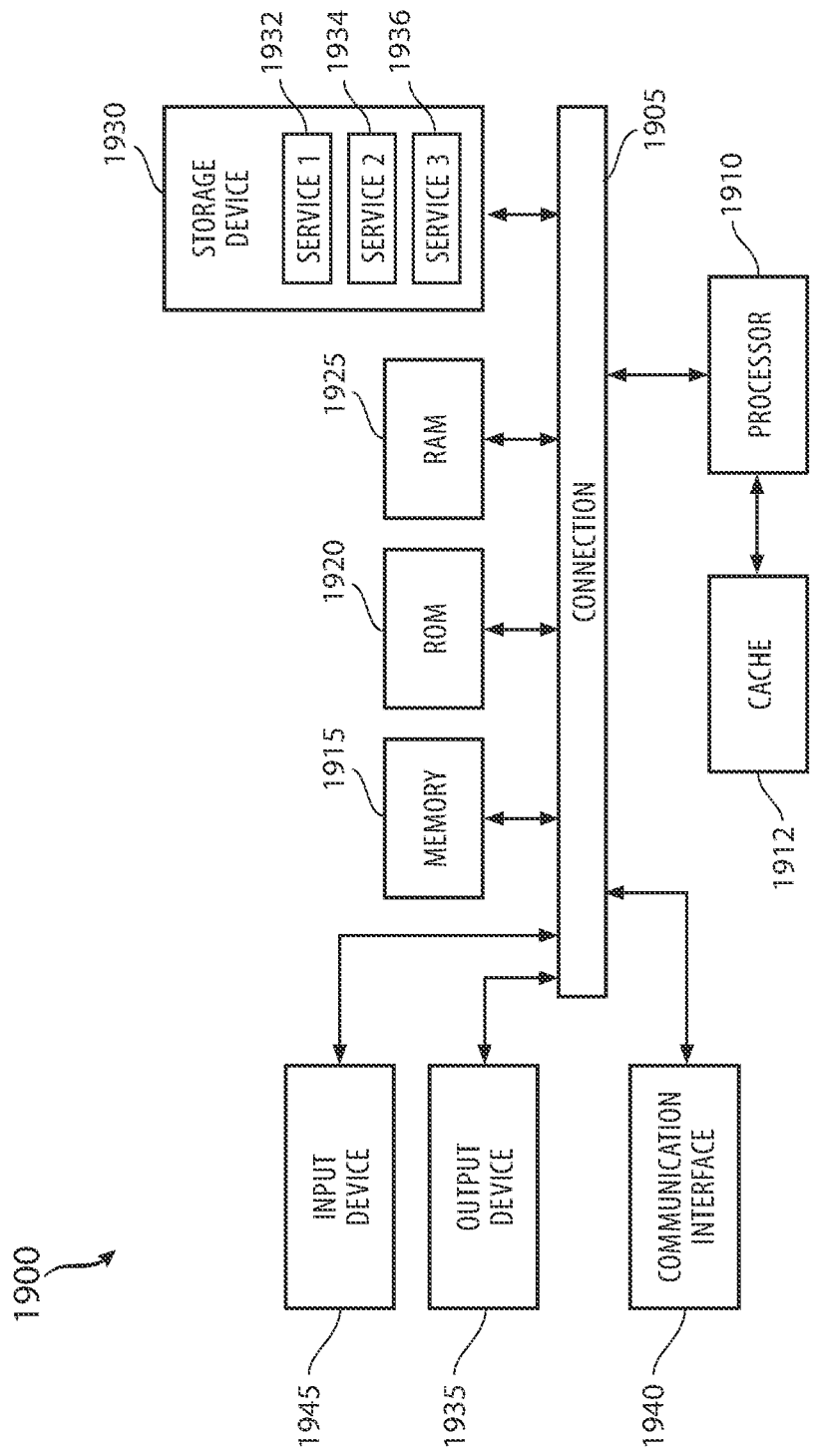
FIG. 19 is a block diagram illustrating an example of a computing system for implementing certain aspects described herein.

FIG. 19 illustrates an example computing device architecture 1900 of an example computing device which can implement the various techniques described herein. In some examples, the computing device can include a mobile device, a personal computer, a laptop computer, a video server, or other device. The components of computing device architecture 1900 are shown in electrical communication with each other using connection 1905, such as a bus. The example computing device architecture 1900 includes a processing unit (CPU or processor) 1910 and computing device connection 1905 that couples various computing device components including computing device memory 1915, such as read only memory (ROM) 1920 and random-access memory (RAM) 1925, to processor 1910.

The computing device architecture 1900 can be used as part of a codec for coding and/or decoding the contact matrix as disclosed herein.

Computing device architecture 1900 can include a cache of high-speed memory connected directly with, in close proximity to, or integrated as part of processor 1910. Computing device architecture 1900 can copy data from memory 1915 and/or the storage device 1930 to cache 1912 for quick access by processor 1910. In this way, the cache can provide a performance boost that avoids processor 1910 delays while waiting for data. These and other engines can control or be configured to control processor 1910 to perform various actions. Other computing device memory 1915 may be available for use as well. Memory 1915 can include multiple different types of memory with different performance characteristics. Processor 1910 can include any general-purpose processor and a hardware or software service, such as service 1 1932, service 2 1934, and service 3 1936 stored in storage device 1930, configured to control processor 1910 as well as a special-purpose processor where software instructions are incorporated into the processor design. Processor 1910 may be a self-contained system, containing multiple cores or processors, a bus, memory controller, cache, etc. A multi-core processor may be symmetric or asymmetric.

To enable user interaction with the computing device architecture 1900, input device 1945 can represent any number of input mechanisms, such as a microphone for speech, a touch-sensitive screen for gesture or graphical input, keyboard, mouse, motion input, speech and so forth. Output device 1935 can also be one or more of a number of output mechanisms known to those of skill in the art, such as a display, projector, television, speaker device, etc. In some instances, multimodal computing devices can enable a user to provide multiple types of input to communicate with computing device architecture 1900. Communication interface 1940 can generally govern and manage the user input and computing device output. There is no restriction on operating on any particular hardware arrangement and therefore the basic features here may easily be substituted for improved hardware or firmware arrangements as they are developed.

Storage device 1930 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1925, read only memory (ROM) 1920, and hybrids thereof. Storage device 1930 can include services 1932, 1934, 1936 for controlling processor 1910. Other hardware or software modules or engines are contemplated. Storage device 1930 can be connected to the computing device connection 1905. In one aspect, a hardware module that performs a particular function can include the software component stored in a computer-readable medium in connection with the necessary hardware components, such as processor 1910, connection 1905, output device 1935, and so forth, to carry out the function.

Aspects of the present disclosure are applicable to any suitable electronic device (such as security systems, smartphones, tablets, laptop computers, vehicles, drones, or other devices) including or coupled to one or more active depth sensing systems. While described below with respect to a device having or coupled to one light projector, aspects of the present disclosure are applicable to devices having any number of light projectors and are therefore not limited to specific devices.

The term "device" is not limited to one or a specific number of physical objects (such as one smartphone, one controller, one processing system and so on). As used herein, a device may be any electronic device with one or more parts that may implement at least some portions of this disclosure. While the below description and examples use the term "device" to describe various aspects of this disclosure, the term "device" is not limited to a specific configuration, type, or number of objects. Additionally, the term "system" is not limited to multiple components or specific embodiments. For example, a system may be implemented on one or more printed circuit boards or other substrates and may have movable or static components. While the below description and examples use the term "system" to describe various aspects of this disclosure, the term "system" is not limited to a specific configuration, type, or number of objects.

Specific details are provided in the description above to provide a thorough understanding of the embodiments and examples provided herein. However, it will be understood by one of ordinary skill in the art that the embodiments may be practiced without these specific details. For clarity of explanation, in some instances the present technology may be presented as including individual functional blocks including functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Individual embodiments may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general-purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as flash memory, memory or memory devices, magnetic or optical disks, flash memory, USB devices provided with non-volatile memory, networked storage devices, compact disk (CD) or digital versatile disk (DVD), any suitable combination thereof, among others. A computer-readable medium may have stored thereon code and/or machine-executable instructions that may represent a procedure, a function, a subprogram, a program, a routine, a subroutine, a module, an engine, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices or other small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language reciting "at least one of" a set and/or "one or more" of a set indicates that one member of the set or multiple members of the set (in any combination) satisfy the claim. For example, claim language reciting "at least one of A and B" or "at least one of A or B" means A, B, or A and B. In another example, claim language reciting "at least one of A, B, and C" or "at least one of A, B, or C" means A, B, C, or A and B, or A and C, or B and C, or A and B and C. The language "at least one of" a set and/or "one or more" of a set does not limit the set to the items listed in the set. For example, claim language reciting "at least one of A and B" or "at least one of A or B" can mean A, B, or A and B, and can additionally include items not listed in the set of A and B.

Any claim included in this application can depend from any one or more claim. Thus, the scope of this disclosure includes any multiple dependent claim structure that is possible.

The various illustrative logical blocks, modules, engines, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, engines, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random-access memory (RAM) such as synchronous dynamic random-access memory (SDRAM), read-only memory (ROM), non-volatile random-access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general-purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein.

What is claimed is:

1. A system comprising:
a processor; and
a computer-readable storage device storing a contact matrix data structure, the contact matrix data structure comprising:
a header containing an interval of a contact matrix, a list of interval multipliers, a tile size, a list of chromosomes with a corresponding identifier and length, a list of sample identifiers, zero or more names of methods of normalization performed on a contact matrix tile;
zero or more bin payload having an interval multiplier;
at least one parameter set; and
at least one matrix payload, wherein the at least one matrix payload comprises one or more tile payload, zero or more precomputed normalized tile payload, zero or one row mask payload and zero or one column mask payload.

2. The system of claim 1, wherein a content of the contact matrix comprises a number of contacts or interactions within a certain genomic region.

3. The system of claim 1, wherein an interval of the contact matrix refers to a bin size of the contact matrix.

4. The system of claim 1, wherein the zero or more names of the method of normalization performed on the contact matrix tile refers to one of an on-the-fly normalization method or a precomputed normalization method.

5. The system of claim 1, wherein the interval multiplier is associated with weights corresponding to a same or higher interval.

6. The system of claim 1, wherein the zero or more bin payload further comprises one or more weights for each of a plurality of on-the-fly normalization methods.

7. The system of claim 1, wherein the interval multiplier comprises a positive integer and is a factor of the tile size.

8. The system of claim 1, wherein the interval multiplier is used in a decoding process by applying the interval multiplier to obtain a summation of all entries within one square window to compute an entry of a contact matrix tile with a higher interval by adding all entries in the one square window.

9. The system of claim 1, wherein the at least one parameter set comprises a parameter set identifier, a first chromosome of a chromosome pair and a second chromosome of the chromosome pair.

10. A method of decoding a contact matrix data structure, the contact matrix data structure comprising: a header containing an interval of a contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payload, wherein the at least one matrix payload comprises one or more tile payload, zero or more precomputed normalized tile payload, zero or one row mask payload and zero or one column mask payload, the method comprising:
  receiving the contact matrix data structure; and
  based on the contact matrix data structure, a desired pair of chromosomes and a desired interval multiplier corresponding to a desired interval of an output contact matrix, generating the output contact matrix.

11. The method of claim 10, wherein the output contact matrix comprises:
  an identifier of sequence 1 chr1_id;
  an array of start position values of sequence 1 start1 [ ];
  an array of end position values of sequence 1 end1 [ ];
  an identifier of sequence 2 chr2_id;
  an array of start position values of sequence 2 start2[ ];
  an array of end position values of sequence 2 end2[ ];
  an array of count values count[ ];
  a 2-dimensional array norm_mats_otf[ ][ ] if a header.num_norm_methods is greater than 1; and
  a 2-dimensional array norm_mats[ ][ ] if a header.num_norm_matrices is greater than 1.

12. The method of claim 11, wherein the chr1_id and the chr2_id each represent a respective identifier of a respective chromosome.

13. The method of claim 11, wherein the header.num_norm_methods is a number of on-the-fly normalization methods for which weights are stored in the zero or more bin payload described in the header.

14. The method of claim 11, wherein the header.num_norm_matrices is a number of precomputed normalized contact matrix described in the header.

15. The method of claim 11, wherein the interval multiplier specifies a multiplier of an interval to compute a number of bin entries.

16. The method of claim 11, wherein the at least one parameter set comprises an identifier parameter set used to decode the at least one matrix payload.

17. The method of claim 10, wherein the one or more tile payload has content depending on a chosen compression method.

18. The method of claim 10, wherein the output contact matrix comprises at least one two-dimensional array tile representing a tile payload.

19. The method of claim 11, wherein the interval multiplier is used to compute larger intervals from a smaller interval contact matrix by:

$$interval\_high = interval\_multplier * interval\_low.$$

20. The method of claim 11, wherein the count[ ] is computed by:
  decoding and transforming tile payload associated to the at least one matrix payload and parameter set;
  summing values within non-overlapping window with window size equals to interval multiplier if the interval multiplier is greater than one to yield results; and
  concatenating all of the results from all tiles.

21. The method of claim 11, wherein the 2-dimensional array norm_mats_otf[ ][ ] is computed by:
  decoding and transforming tile payload associated to the at least one matrix payload and the at least one parameter set;
  summing values within non-overlapping window with window size equals to interval multiplier if the interval multiplier is greater than one; and
  multiplying with weights stored in the zero or more bin payload by:
  $T\_i\_j = w\_i * w\_j * A\_i\_j$ if an associated norm_methods_mult_flag is 1, otherwise $T\_i\_j = A\_i\_j / (w\_i * w\_j)$ to yield results;
  concatenating all of the results from all tiles.

22. The method of claim 19, wherein the interval_multiplier is a positive integer and a factor of a tile size associated with the at least one matrix payload.

23. The method of claim 19, wherein the interval_low is the interval described in the header.

24. The method of claim 19, wherein the interval_high is the desired interval.

25. The method of claim 21, wherein the A_i_j is a value of a 2-dimensional array tile at row i and column j.

26. The method of claim 21, wherein the w_i is an i-th weight of an associated on-the-fly normalization method.

27. The method of claim 21, wherein the w_j is a j-th weight of an associated on-the-fly normalization method.

28. The method of claim 21, wherein the T_i_j is a value of a 2-dimensional array normalized tile at row i and column j.

29. A system comprising:
  a processor; and
  a computer-readable storage device storing a contact matrix, related information and program instructions wherein the program instructions, when executed by the processor, cause the processor to perform operations comprising:
    receiving the contact matrix from the computer-readable storage device; and
    based on the contact matrix, generating a contact matrix structure, wherein the contact matrix structure comprises: a header containing an interval of the contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payload, wherein the at least one matrix payload comprises one or more tile payload, zero or more precomputed normalized tile payload, zero or one row mask payload and zero or one column mask payload.

30. A method of coding a contact matrix data structure from a contact matrix, the contact matrix data structure comprising: a header containing an interval of a contact matrix, a list of interval multipliers, a tile size, a list of chromosomes with a corresponding identifier and length, a list of sample identifiers, zero or more names of methods of normalization performed on a contact matrix tile; zero or more bin payload having an interval multiplier; at least one parameter set; and at least one matrix payload, wherein the at least one matrix payload comprises one or more tile payload, zero or more precomputed normalized tile payload, zero or one row mask payload and zero or one column mask payload, the method comprising:
  receiving the contact matrix; and
  based on the contact matrix, generating the contact matrix data structure.

* * * * *